(12) United States Patent
Cecchetto et al.

(10) Patent No.: US 9,962,850 B2
(45) Date of Patent: May 8, 2018

(54) APERTURED WEB

(71) Applicant: The Procter & Gamble Company, Cincinnati, OH (US)

(72) Inventors: Pietro Cecchetto, Fairfield, OH (US); Xue Wang, Beijing (CN); Jan Fuhrmann-Evers, Frankfurt am Main (DE)

(73) Assignee: The Procter & Gamble Company, Cincinnati, OH (US)

( * ) Notice: Subject to any disclaimer, the term of this patent is extended or adjusted under 35 U.S.C. 154(b) by 79 days.

(21) Appl. No.: 14/731,986

(22) Filed: Jun. 5, 2015

(65) Prior Publication Data
US 2016/0038351 A1   Feb. 11, 2016

(51) Int. Cl.
| | |
|---|---|
| *B26F 1/20* | (2006.01) |
| *A61F 13/512* | (2006.01) |
| *B29C 51/08* | (2006.01) |
| *B29C 51/20* | (2006.01) |
| *B29C 51/10* | (2006.01) |
| *B29C 51/26* | (2006.01) |
| *B29K 101/12* | (2006.01) |

(Continued)

(52) U.S. Cl.
CPC .......... *B26F 1/20* (2013.01); *A61F 13/5121* (2013.01); *A61F 13/5126* (2013.01); *B29C 51/082* (2013.01); *B29C 51/20* (2013.01); *A61F 2013/5127* (2013.01); *B29C 51/10* (2013.01); *B29C 51/266* (2013.01); *B29K 2101/12* (2013.01); *B29L 2009/00* (2013.01); *B29L 2031/7128* (2013.01); *B29L 2031/756* (2013.01); *Y10T 428/24281* (2015.01)

(58) Field of Classification Search
CPC .............. A61F 13/5126; A61F 13/5121; A61F 2013/5127; Y10T 428/24281
See application file for complete search history.

(56) References Cited

U.S. PATENT DOCUMENTS

| | | | |
|---|---|---|---|
| 5,158,819 | A | 10/1992 | Goodman et al. |
| 5,591,149 | A | 1/1997 | Cree et al. |

(Continued)

FOREIGN PATENT DOCUMENTS

| | | |
|---|---|---|
| JP | 2741821 B2 | 4/1998 |

OTHER PUBLICATIONS

PCT International Search Report, mailed 12 May 2015, 20 pp.
PCT Supplementary International Search Report, dated Nov. 23, 2016, 194 pages.

*Primary Examiner* — William P Watkins, III
(74) *Attorney, Agent, or Firm* — George H. Leal; Andrew J. Hagerty

(57) ABSTRACT

The present invention relates to a web comprising: discrete extended elements having open proximal ends, open or closed dismal ends and side walls; macro apertures arranged in a staggered pattern; first regions comprising a first top plane; and second regions comprising a second top plane having a length less than or equal to about 0.9 mm, wherein each of the first regions is surrounded by four distinctive second regions, the four distinctive second regions being connected by two adjacent macro apertures in the first direction and another two adjacent macro apertures in the second direction which is orthogonal to the first direction, and wherein each of the second regions is surrounded by two adjacent first regions and two adjacent macro apertures located in a third direction or a fourth direction not parallel either to the first direction or to the second direction.

20 Claims, 13 Drawing Sheets

(51) Int. Cl.
*B29L 31/00* (2006.01)
*B29L 9/00* (2006.01)

(56) References Cited

U.S. PATENT DOCUMENTS

| | | |
|---|---|---|
| 5,770,144 A | 6/1998 | James et al. |
| 5,895,380 A | 4/1999 | Turi et al. |
| 6,228,462 B1 | 5/2001 | Lee et al. |
| 2004/0119207 A1 | 6/2004 | Stone et al. |
| 2010/0036346 A1 | 2/2010 | Hammons et al. |
| 2010/0201024 A1 | 8/2010 | Gibson et al. |
| 2011/0221094 A1 | 9/2011 | Gross et al. |
| 2011/0223388 A1 | 9/2011 | Stone et al. |
| 2012/0273997 A1 | 11/2012 | Stone et al. |

APERTURED WEB

FIELD OF THE INVENTION

The present invention is directed to web materials having microtextures and macro apertures, and absorbent articles comprising such web materials.

BACKGROUND OF THE INVENTION

Webs, such as thermoplastic films, have a variety of uses including component materials of absorbent articles (such as topsheets and backsheets), packaging (such as flow wrap, shrink wrap, and polybags), trash bags, food wrap, dental floss, wipes, electronic components, and the like. For many of these uses of webs, it can be beneficial for the web to have a textured, three-dimensional surface which can provide the surface of the web with a desirable feel (e.g., soft, silky), visual impression, and/or audible impression, as well as one or more desirable properties such as improved fluid handling.

Webs exhibiting a desirable feel can be made by forming microtextures such as protrusions and recessions in the webs via technologies such as a vacuum forming process, hydroforming process and embossing process. With a typical vacuum forming process, a precursor web is heated and placed over a forming structure. Then a vacuum of air forces the precursor web to conform to the texture of the forming structure. With a typical hydroforming process, a precursor web is placed over a forming structure and high pressure and high temperature water jets force the precursor web to conform to the texture of the forming structure.

Micro-textured webs can be further deformed to have three-dimensionally macro apertures fluid transportation structures for improved fluid handling. Macro-apertured webs are utilized in a wide variety of industrial and consumer products. For example, apertured webs are known for use in disposable absorbent articles such as disposable diapers and feminine hygiene articles such as sanitary napkins, and the like. Such articles typically have a fluid pervious topsheet, a fluid impervious breathable backsheet, and an absorbent core disposed between the topsheet and the backsheet. An apertured web can be made to form a fluid pervious topsheet and/or the fluid impervious breathable backsheet.

Even with formation of macro apertures for fluid transportation in a micro-textured web, there still is a challenge in fluid drainage as there are flat areas in the web. Especially when microtextures are in the form of discrete extended elements like protrusions, fluid is trapped in valleys among the discrete extended elements. In addition, discrete extended elements are rather fragile, once micro-texturing is completed, it is difficult to create apertures by mechanical deformation such as hot roll as the heat from the hot roll may melt parts of the discrete extended elements and impart permanent deformation into the discrete extended elements. For example, the heat can cause end edges of discrete extended elements crisp to become very stiff as a result of the exposure to the heat. The crisp or stiffened edges make final products using the web such as absorbent articles rough to the skin.

Therefore, a need exists for a web having both microtextures and macro apertures with enhanced fluid drainage.

Therefore, another need exists for a web having both microtextures and macro apertures without compromising desirable softness.

SUMMARY OF THE INVENTION

The present invention is directed to apertured webs exhibiting an improved fluid handling property and desirable softness, comprising a) discrete extended elements, b) macro apertures arranged in a staggered pattern, c) first regions, and d) second regions, wherein the second regions comprise a second top plane having a length less than or equal to about 0.9 mm as measured according to Top Plane length Measurement.

The present invention is also directed to apertured webs exhibiting an improved fluid handling property and desirable softness, comprising a) discrete extended elements, b) macro apertures arranged in a staggered pattern, c) first regions, and d) second regions, wherein the second regions have better fluid drainage than the first regions.

The present invention is also directed to apertured webs comprising discrete extended elements substantially intact from heat damage.

The present invention is also directed to an absorbent article having a topsheet comprising a web according to the present invention.

Figure 1A:
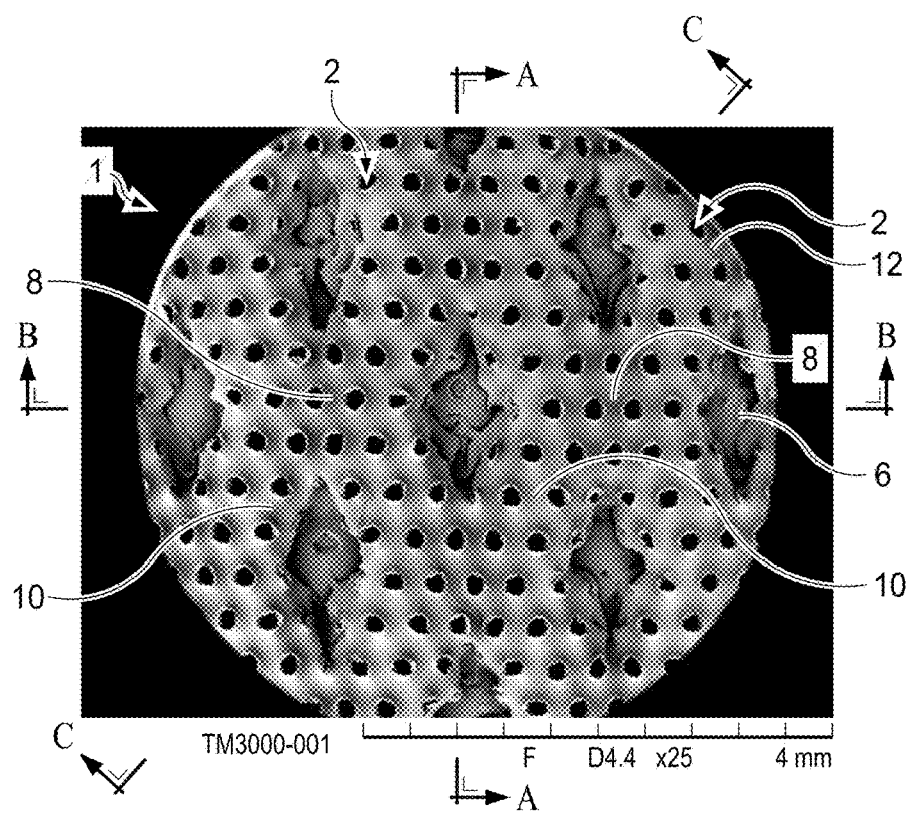
FIG. 1A is a plan view scanning electron microscope image of one embodiment of film according to the present invention.

The embodiments shown in the drawings are illustrative in nature and are not intended to be limiting of the invention defined by the claims. Moreover, the features of the invention will be more fully apparent and understood in view of the detailed description.

DETAILED DESCRIPTION

The term "absorbent article" includes disposable articles such as sanitary napkins, panty liners, tampons, interlabial devices, wound dressings, diapers, adult incontinence articles, wipes, and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. Various absorbent articles described above will typically comprise a liquid pervious topsheet, a liquid impervious backsheet joined to the topsheet, and an absorbent core between the topsheet and backsheet.

The term "absorbent core", as used herein, refers to the component of the absorbent article that is primarily responsible for storing liquids. As such, the absorbent core typically does not include the topsheet or backsheet of the absorbent article.

The term "adjacent", as used herein, with reference to features or regions, means near or close to, and which need not be in contact with each other.

The term "aperture", as used herein, refers to a hole. The apertures can either be punched cleanly through the web so that the material surrounding the aperture lies in the same plane as the web prior to the formation of the aperture (a "two dimensional" aperture), or holes formed in which at least some of the material surrounding the opening is pushed out of the plane of the web. In the latter case, the apertures may resemble a protrusion or depression with an aperture therein, and may be referred to herein as a "three dimensional" aperture, a subset of apertures.

The term "component" of an absorbent article, as used herein, refers to an individual constituent of an absorbent article, such as a topsheet, acquisition layer, liquid handling layer, absorbent core or layers of absorbent cores, backsheets, and barriers such as barrier layers and barrier cuffs.

The term "cross-machine direction" or "CD", as used herein, refers to the path that is perpendicular to the machine direction in the plane of the web.

The term "deformable" material, as used herein, is a material which is capable of changing its shape or density in response to applied stresses or strains.

The term "discrete", as used herein, means distinct or unconnected. When the term "discrete" is used relative to forming elements on a forming member, it is meant that the distal (or radially outwardmost) ends of the forming elements are distinct or unconnected in all directions, including in the machine and cross-machine directions (even though bases of the forming elements may be formed into the same surface of a roll, for example).

The term "forming elements", as used herein, refers to any elements on the surface of a forming member that are capable of deforming a web.

The term "layer" used herein should be understood that the term "layer" is not necessarily limited to single layers or sheets of material. Thus the layer can comprise laminates or combinations of several sheets or webs of the requisite type of materials. Accordingly, the term "layer" includes the terms "layers" and "layered".

The term "machine direction" or "MD", as used herein, refers to the path that material, such as a web, follows through a manufacturing process.

The term "macroscopic" or "macro", as used herein, refers to structural features or elements that are readily visible and distinctly discernable to a human having 20/20 vision when the perpendicular distance between the viewer's eye and the web is about 12 inches (30 cm). Conversely, the term "microscopic" or "micro" refers to such features that are not readily visible and distinctly discernable under such conditions.

The terms "mechanical deformation", as used herein, refers to processes in which a mechanical force is exerted upon a material to form two-dimensional or three-dimensional structures on a web.

The term "surrounded", as used herein, refers to both being completely and continuously surrounded, and being discontinuously surrounded by other regions and/or apertures.

Apertured Web

Figure 1B:
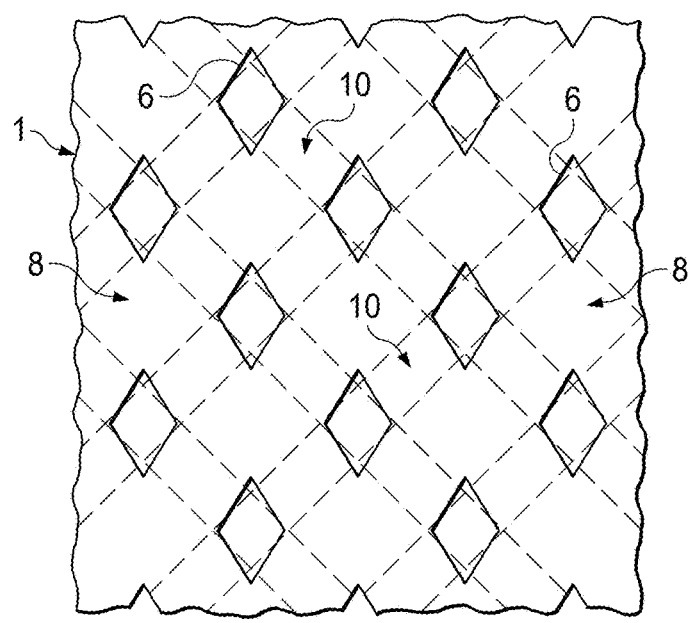
FIG. 1B is a schematic representation of the film of FIG. 1A.

FIGS. 1A and 1B are a magnified exemplary three-dimensional apertured film web 1 and its schematic representation, respectively. Referring to FIGS. 1A and 1B, the apertured web 1 according to the present invention comprises a plurality of discrete extended elements 2 (not indicated in FIG. 1B) extended outwardly from a first surface 12 of the web 1, a plurality of spaced apart macro apertures 6, a plurality of first regions 8, and a plurality of second regions 10.

The web according to the present invention has improved softness. As shown in FIG. 1A of a plan view scanning electron microscope image of film according to the present invention and FIGS. 2A-2C of cross section views of the film of FIG. 1, the web of the present invention has substantially intact discrete extended elements 2 without substantial heat damage. Without wishing to be bound by any particular theory, it is believed that undamaged discrete extended elements on a surface of a web can provide to the skin when the web is intended to form at least a portion of the wearer-facing surface of an absorbent article and the surface of the web is in at least partial contact with the skin of a wearer.

Figure 1C:
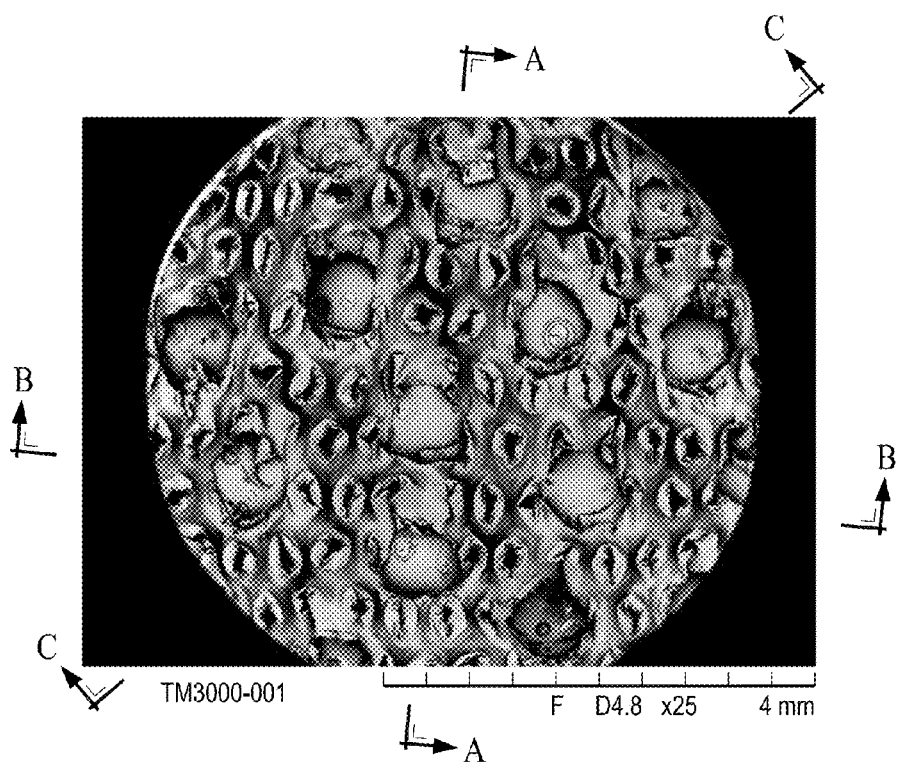
FIG. 1C is a plan view scanning electron microscope image of film topsheet of a commercially available sanitary napkin.
Figure 1D:
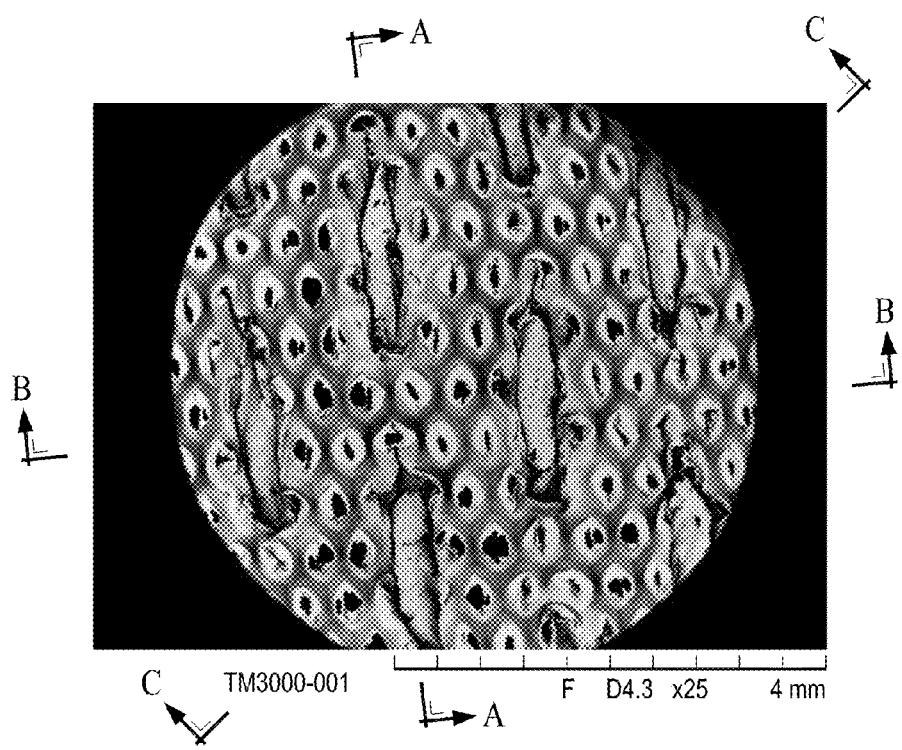
FIG. 1D is a plan view scanning electron microscope image of film topsheet of another commercially available sanitary napkin.
Figure 1E:
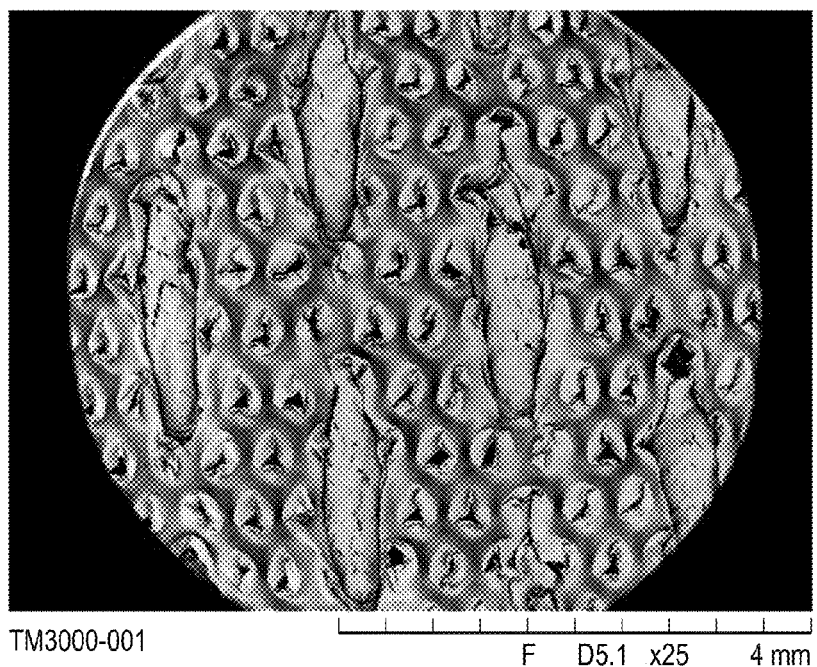
FIG. 1E is a plan view scanning electron microscope image of film topsheet of commercially available marketed sanitary napkin.

FIGS. 1C-1E are plan view scanning electron microscope images of film topsheets of commercial sanitary pads (FIG. 1C: Kotex U, Kimberly Clark, Singapore; FIG. 1D: Lilian, Kleannara Co. Ltd, Korea; and FIG. 1E: 7 Space Teens, Hengan Industrial Co. Ltd, China) showing apertures and significantly damaged micro structures.

Each of the first regions 8 is surrounded by four distinctive second regions 10. The four distinctive second regions 10 surrounding the each of the first regions 8 are connected by two adjacent macro apertures 6 located along a first direction and another two adjacent macro apertures 6 located long a second direction which is orthogonal to the first direction. Each of the second regions 10 is surrounded by two adjacent first regions 8, and two adjacent macro apertures 6 located either along a third direction or along a fourth direction either of which is not parallel either to the first direction or to the second direction.

Referring to FIG. 1A and FIGS. 2A-2C, the second regions 10 comprise a second top plane 11 in the second direction having a second top plane length in the third direction or the fourth direction shorter than a length of a first plane 9 of the first regions 8 in the first direction. In one embodiment, the second regions comprise a second top plane having a length in the third direction or fourth direction less than or equal to about 0.9 mm between the two adjacent macro apertures as measured according to Top Plane length Measurement described later. In another embodiment, the second regions 10 have better fluid drainage than the first regions 8. As seen FIG. 3A the web according to the present invention shows enhanced fluid drainage. Without wishing to be bound by any particular theory, it is believed that the short top plane length of the second regions is effective to drain fluid and prevent the fluid from being trapped in valleys between micro structures such as discrete extended elements. FIGS. 3B-3D are plan view scanning electron microscope images of film topsheets showing Fluid Drainage Test results (FIG. 3B: Kotex U, Kimberly Clark, Singapore; FIG. 3C: Lilian, Kleannara Co. Ltd, Korea, and FIG. 3D: 7 Space Teens, Hengan Industrial Co. Ltd, China).

Figure 2A:
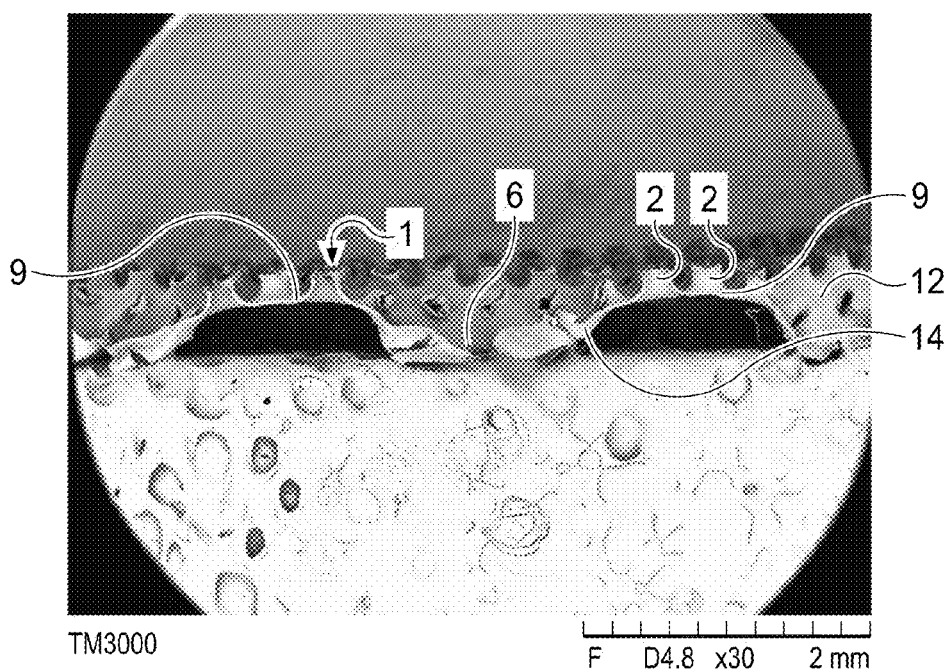
FIG. 2A is a scanning electron microscope image of the A-A direction cross section of the film of FIG. 1A.
Figure 2B:
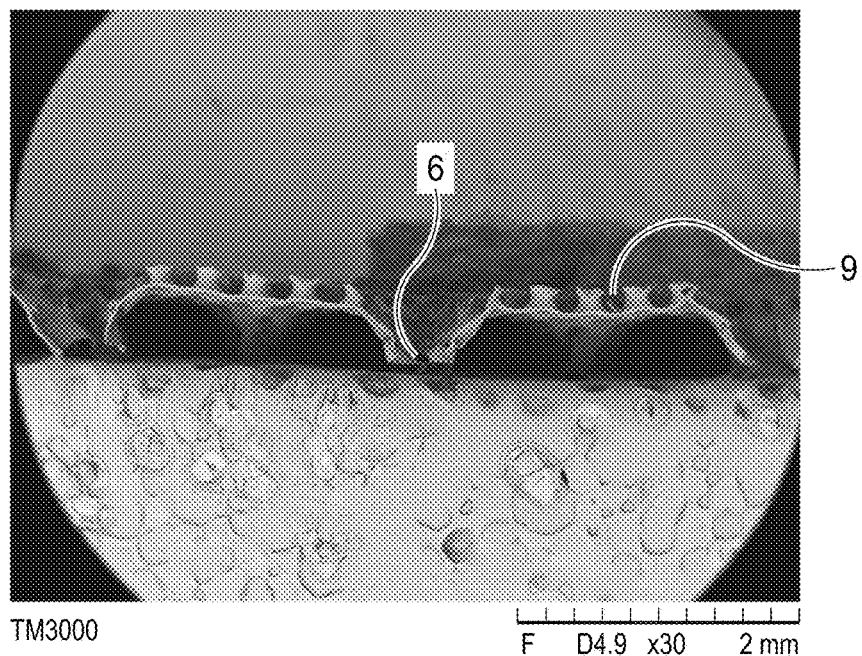
FIG. 2B is a scanning electron microscope image of a B-B direction cross section of the film of FIG. 1A.
Figure 2C:
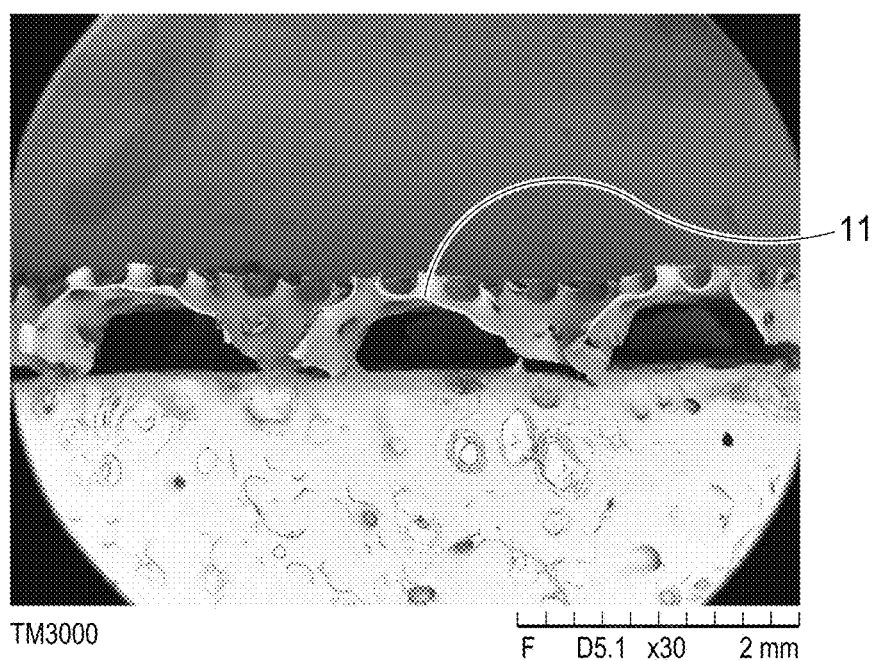
FIG. 2C is a scanning electron microscope image of a C-C direction cross section of the film of FIG. 1A.
Figure 3B:
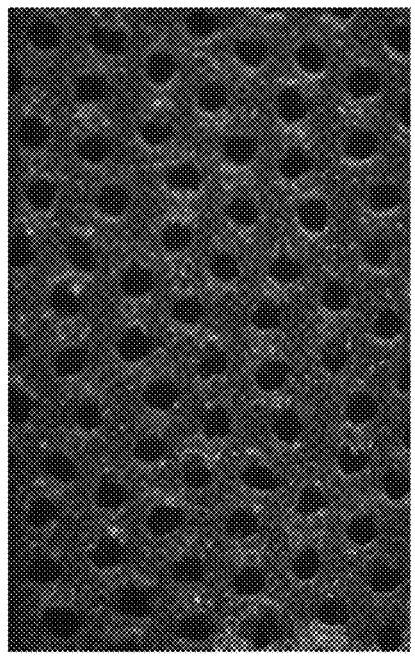
FIG. 3B is a plan view scanning electron microscope image of the film topsheet of FIG. 1C in Fluid Drainage Test.
Figure 3D:
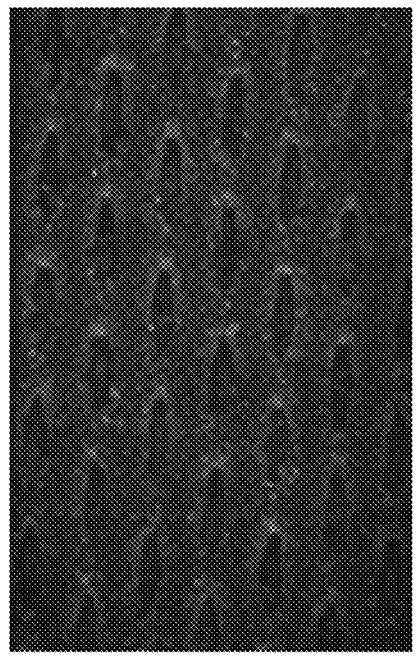
FIG. 3D is a plan view scanning electron microscope image of the film topsheet of FIG. 1E in Fluid Drainage Test.
Figure 3A:
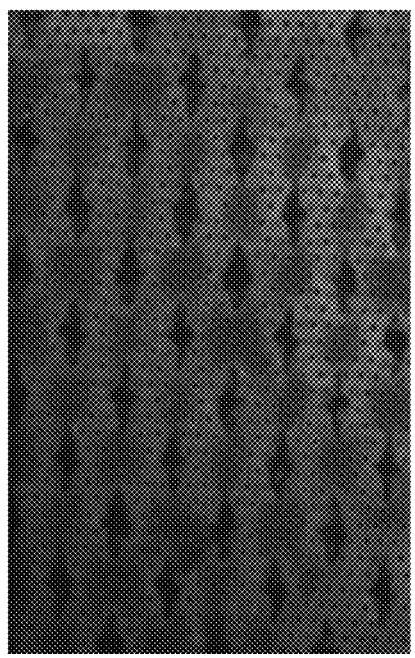
FIG. 3A is a plan view scanning electron microscope image of the film of FIG. 1A in Fluid Drainage Test.
Figure 3C:
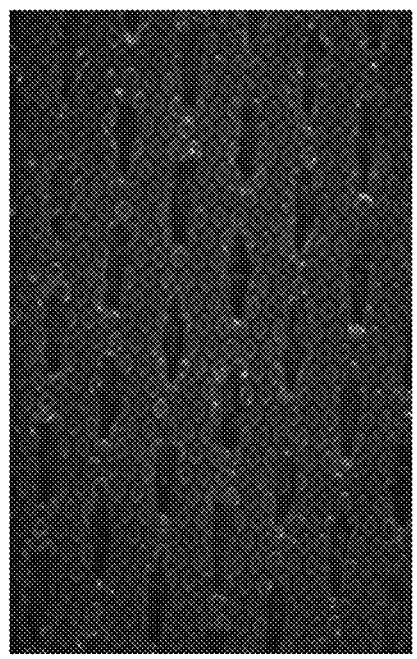
FIG. 3C is a plan view scanning electron microscope image of the film topsheet of FIG. 1D in Fluid Drainage Test.

As shown in FIGS. 2A-2C, apertures 6 extend away from a second surface 14 of web 1 while discrete extended elements 2 extend away from first surface 12 of web 1, so that the apertures 6 and the discrete extended elements 2 are formed in the opposite direction.

In another non-limiting embodiment, the apertured web further comprises a plurality of spaced apart deformed features such as apertures ("second apertures") different from the first apertures in terms of one or more of the following properties shape, size, aspect ratio, center-to-center spacing, height or depth, density, color, surface treatment (e.g., lotion, etc.), number of web layers within the features, and orientation (protruding from different sides of the web).

The web 1 may be a single layer web made from a single layer precursor web, a laminate or composite precursor web having two or more layers or plies. In general, a web 1 formed from a laminate precursor web could be comprised of apertures 6 wherein sidewalls of the apertures 6 comprise one or more of the precursor web materials.

Multilayer apertured webs 1 made from composite laminate precursor webs may have advantages over single layer apertured webs 1 in a certain aspect. For example, an aperture 6 from a multilayer apertured web 1 using two precursor webs can comprise fibers (in the case of nonwoven webs) or stretched film (in the case of film webs) in a "nested" relationship that "locks" the two precursor webs together. One advantage of the locking configuration is that, while adhesives or thermal bonding may be present, the nesting allows forming a laminate web without the use or need of adhesives or additional thermal bonding between the layers. In other embodiments, multilayer webs can be chosen such that the fibers in a nonwoven web layer have greater extensibility than an adjacent film layer. Such webs can produce apertures 6 by pushing fibers from a nonwoven layer up and through an upper film layer which contributes little or no material to sidewalls.

In a multilayer apertured web 1 each precursor web can have different material properties, thereby providing apertured web 1 with beneficial properties. For example, apertured web 1 comprising two (or more) precursor webs, e.g., first and second precursor webs can have beneficial fluid handling properties for use as a topsheet on a disposable absorbent article. For superior fluid handling on a disposable absorbent article, for example, second precursor web can form an upper film layer (i.e., a body-contacting surface when used as a topsheet on a disposable absorbent article) and be comprised of relatively hydrophobic polymer. First precursor web can be a nonwoven fibrous web and form a lower layer (i.e., disposed between the topsheet and an absorbent core when used on a disposable absorbent article) comprised of relatively hydrophilic fibers. Fluid deposited upon the upper, relatively hydrophobic layer can be quickly transported to the lower, relatively hydrophilic, layer. For some applications of disposable absorbent articles, the relative hydrophobicity of the layers could be reversed, or otherwise modified. In general, the material properties of the various layers of apertured web 1 can be changed or modified by means known in the art for optimizing the fluid handling properties of apertured web 1.

It should be understood that while the term "apertured web" is utilized herein, the object is to create components for absorbent articles from such apertured web. In such cases, the apertured web will be cut into individual components for absorbent articles. The apertured web can also be used in products other than absorbent articles.

Web Material

A web of the present invention can comprise any suitable deformable material, such as a woven, nonwoven, polymeric film, combination, or laminate of any of the foregoing materials.

The web can be a polymeric film web. Polymeric film webs can be deformable. Deformable, as used herein, describes a material which, when stretched beyond its elastic limit, will substantially retain its newly formed conformation. Such deformable materials may be chemically homogeneous or heterogeneous, such as homopolymers and polymer blends, structurally homogeneous or heterogeneous, such as plain sheets or laminates, or any combination of such materials.

Deformable polymeric film webs that can be used can have a transformation temperature range in which changes in the solid state molecular structure of the material occur. Changes in the structure can include a change in crystalline structure and/or a change from solid to molten state. As a consequence, above the transformation temperature range, certain physical properties of the material are substantially altered. For a thermoplastic film, the transformation temperature range is the melt temperature range of the film, above which the film is in a molten state and loses substantially all previous thermo-mechanic al history.

Polymeric film webs can comprise thermoplastic polymers having characteristic rheological properties which depend on their composition and temperature. Below their glass transition temperature, such thermoplastic polymers can be hard, stiff, and/or brittle. Below the glass transition temperature, the molecules are in rigid, fixed positions. Above the glass transition temperature but below the melt temperature range, thermoplastic polymers exhibit viscoelasticity. In this temperature range, the thermoplastic material generally has a certain degree of crystallinity, and is generally flexible and to some degree deformable under a force. The deformability of such a thermoplastic is dependent on the rate of deformation, amount (dimensional quantity) of deformation, length of time it is deformed, and its temperature. In one embodiment, processes can be utilized to form materials comprising thermoplastic polymers, especially thermoplastic film, which are within this viscoelastic temperature range.

Polymeric film webs can comprise a certain amount of ductility. Ductility, as used herein, is the amount of permanent, unrecoverable, plastic strain which occurs when a material is deformed, prior to failure (rupture, breakage, or separation) of the material. Materials that can be used as described herein can have a minimum ductility of at least about 10%, or at least about 50%, or at least about 100%, or at least about 200%.

Polymeric film webs can include materials normally extruded or cast as films such as polyolefins, nylons, polyesters, and the like. Such films can be thermoplastic materials such as polyethylene, low density polyethylene, linear low density polyethylene, polypropylenes and copolymers and blends containing substantial fractions of these materials. Such films can be treated with surface modifying agents to impart hydrophilic or hydrophobic properties, such as imparting a lotus effect. As noted below, polymeric film webs can be textured or otherwise altered from a strictly flat, planar configuration.

The web of the present invention can be a nonwoven web. As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing, spunbonding, hydroentangling, airlaid, wetlaid, through-air-dried paper making processes, and bonded carded web processes, including carded thermal bonding. The nonwoven webs can comprise unbonded fibers, entangled fibers, tow fibers, or the like. Fibers can be extensible and/or elastic, and may be pre-stretched for processing. Fibers can be continuous, such as those produced by spunbonded methods, or cut to length, such as those typically utilized in a carded process. Fibers can be absorbent, and can include fibrous absorbent gelling materials. Fibers can be bicomponent, multiconstituent, shaped, crimped, or in any other formulation or configuration known in the art for nonwoven webs and fibers. The nonwoven webs comprising polymer fibers having sufficient elongation properties to be formed into an apertured web. In general, the polymeric fibers can be bondable, either by chemical bond (e.g. by latex or adhesive bonding), pressure bonding, or thermal bonding. If thermal bonding techniques are used in the bonding process described below, a certain percentage of thermoplastic material, such as thermoplastic powder or fibers can be used The web of the present invention can be a composite or a laminate of two or more precursor webs, and can comprise two or more nonwoven webs or a combination of polymer films, nonwoven webs, woven fabrics, paper webs, tissue webs, or knitted fabrics. In general, a web formed from a laminate precursor web could be comprised of apertures 6 wherein sidewalls of the apertures 6 comprise one or more of the precursor web materials.

The web can also optionally include colorants, such as pigment, lake, toner, dye, ink or other agent used to impart a color to a material, to improve the visual appearance of an apertured web. Suitable pigments herein include inorganic pigments, pearlescent pigments, interference pigments, and the like.

Discrete Extended Elements

The web of the present invention comprises a plurality of discrete extended elements comprising open proximal ends, open or closed distal ends, and sidewalls.

The discrete extended elements have a diameter shorter than a minor axis of macro apertures formed in the web of the present invention. In one non-limiting embodiment, the discrete extended elements have a diameter of less than about 500 microns; the discrete extended elements have an aspect ratio of at least about 0.2; and/or the web comprises at least about 95 discrete extended elements per square centimeter.

The discrete extended elements can also be aperture protrusions, non-apertured protrusions or fibrils to provide texture that provides for a tactile impression of softness. Softness is beneficial when webs are used as topsheets in disposable absorbent articles. Referring to FIG. 1A and FIGS. 2A-2C, the web according to the present invention is effective in preserving the micro texture discrete extended elements 2, particularly when the macro apertures 6 are made on the disposable absorbent article production line. In this manner, a soft, compliant topsheet for a disposable absorbent article can be achieved when the apertured web is used with the second surface 14 of web 1 having the discrete extended elements 2 as the body-facing surface of the article.

Patent publications disclosing such a plurality of discrete extended elements include WO 01/76842; WO 10/104996; WO 10/105122; WO 10/105124 and US20120277701A1.

The web with discrete extended elements can be provided using any process known in the art. Providing the web with discrete extended elements will provide the exterior surfaces of the web with a softer, more cloth-like texture, provide the web with a more cloth-like appearance, and increase the overall caliper of the web. Examples of discrete extended elements processes include but are not limited to the following: hydroforming, vacuum forming, mechanical deformation, flocking, ultrasonics, delamination of viscous melts from porous surfaces, printed hair, brushing, and any combination thereof.

In one embodiment, three dimensional surface structures comprising discrete extended elements are formed by applying a high pressure fluid jet comprised of water or the like against one surface of the formed web ply, preferably while applying a vacuum adjacent the opposite surface of the formed web ply. In general, the formed web ply is supported on one layer of a forming structure having opposed layers. The forming structure is provided with a multiplicity of apertures there through which place the opposed layers in fluid communication with one another. Such methods of aperturing are known as "hydroformation" and are described in greater detail in U.S. Pat. Nos. 4,609,518; 4,629,643; 4,637,819; 4,681,793; 4,695,422; 4,778,644; 4,839,216; and 4,846,821.

Vacuum formation is disclosed in U.S. Pat. No. 4,463, 045.

Examples of mechanical deformation is disclosed in U.S. Pat. Nos. 4,798,604, 4,780,352, 3,566,726, 4,634,440, WO 97/40793, and European Patent 525,676.

Examples of flocking are disclosed in WO 98/42289, WO 98/36721, and European Patent 861,646.

Examples of ultrasonics are disclosed in U.S. Pat. No. 5,269,981.

Examples of delamination of viscous melts are disclosed in U.S. Pat. No. 3,967,623, and WO 99/06623.

Examples of printed hair are disclosed in U.S. Pat. No. 5,670,110.

Examples of brushing are disclosed in WO 99/06623.

Macro Apertures

The web according to the present invention comprises a plurality of macro apertures. The macro apertures may be planar and two dimensional or three dimensional. "Planar" and "two dimensional" is meant simply that the web is flat relative to apertured web 1 that has distinct, out-of-plane, Z-direction three-dimensionality imparted due to the formation of apertures 6 with sidewalls. "Planar" and "two-dimensional" are not meant to imply any particular flatness, smoothness or dimensionality. In one embodiment, the web according to the present invention comprises a plurality of three dimensional macro apertures. Referring to FIG. 1A, macro apertures 6 formed on a web 1 can be extended outwardly from the second surface 14 of the web 1, the macro apertures 6 having a major axis dimension and a minor axis dimension and being arranged in a staggered pattern. The macro apertures 6 in the web 1 are extended the opposite the direction discrete extended elements are extended.

The macro apertures are discrete, and may be of any suitable configuration. Suitable configurations for the apertures include, but are not limited to: columnar shapes; dome-shapes, tent-shapes, volcano-shapes; features having plan view configurations including circular, oval, hour-glass shaped, star shaped, polygonal and the like, and combinations thereof. "Polygonal" herein intends to include polygonal with rounded corners. Polygonal shapes include, but are not limited to triangular, quadrilateral, hexagonal, octagonal or trapezoidal. In some embodiments, the first and/or second features may exclude one or more of the configurations listed above. In one embodiment, the macro apertures are substantially quadrilateral including rectangular, square, and lozenge shape. The macro apertures may have a ratio of a major axis dimension to minor axis dimension of not greater than 3.3, or not greater than 2.5, or not greater than 2, or not greater than 1.9. In another embodiment, the major axis of the macro apertures is substantially parallel to the MD of an apertured web. In another embodiment, the major axis of the macro apertures is substantially parallel to the CD of an apertured web. In another embodiment, the major axis of the macro apertures is oriented at an angle relative to the MD. Despite the terms of 'major" and "minor" axes, it is intended that a major axis and a minor axis can have an identical length.

In one embodiment, the macro apertures have a quadrilateral shape such as a rectangular, square, and lozenge shape.

The plan view area of the individual macro aperture, in some embodiments of the web, be greater than or equal to about 0.5 mm$^2$, 1 mm$^2$, 5 mm$^2$, 10 mm$^2$, or 15 mm$^2$, or lie in any range between the macro apertures. The number of apertures 6 per unit area of apertured web 1, i.e., the area density of apertures 6, can be varied from about 5-60 apertures per square centimeter. In one embodiment, the web 1 comprises macro apertures with a macro aperture density of from about 10 to about 50, or from about 20 to about 40 apertures/cm$^2$ web. There can be at least 20 apertures 6 per square centimeter, depending on the end use. In general, the area density need not be uniform across the entire area of apertured web 1, but apertures 6 can be only in certain regions of apertured web 1, such as in regions having predetermined shapes, such as lines, stripes, bands, circles, and the like. In one embodiment, where apertured web 1 is used as a topsheet for a sanitary napkin, for example, apertures 6 can be only in the region corresponding to the central part of the pad where fluid entry occurs.

Figure 4:
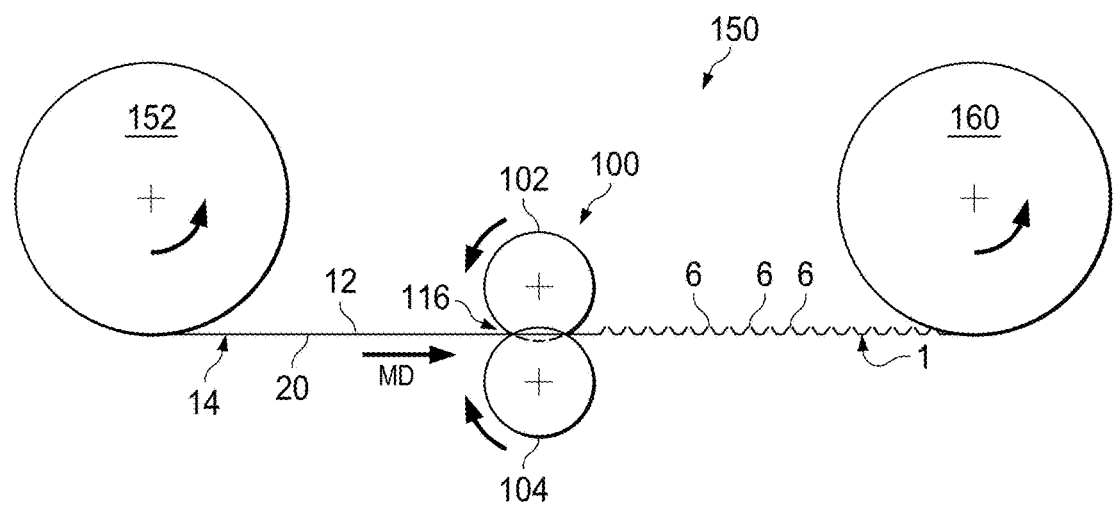
FIG. 4 is a schematic representation of a process for forming a web having macro apertures.

The apertures 6 of the film embodiment shown in FIG. 1A was formed by a process and an apparatus like those shown in FIG. 4, where the apparatus 100 is arranged to have one patterned male roll, e.g., roll 104, and one mating female roll 102.

In one embodiment, it may be possible to have multiple apparatuses 100 such that apertured web 1 is re-processed to have additional apertures 6. For example, a higher area density of aperture 6 on apertured web 1 can be achieved by processing precursor web 20 through two or more apparatuses 100.

As can be understood with respect to forming apparatus 100 shown in FIG. 4, therefore, apertures 6 of apertured web 1 are made by mechanically deforming precursor web 20 that can be described as generally three dimensional. As precursor web 20 goes through the nip 116, the teeth 110 of roll 104 engages recesses 108 of roll 102 and simultaneously urge material out of the plane of precursor web 20 to form permanent apertures 6. In effect, teeth 110 "push" or "punch" through precursor web 20. As the tip of teeth 110 push through precursor web 20, the web material is urged by the teeth 110 out of the plane of precursor web 20 and is stretched and/or plastically deformed in the Z-direction, resulting in formation of apertures 6. The amount of ductility and other material properties of the precursor web, such as the glass transition temperature and crystallinity determine how much relatively permanent three-dimensional deformation the apertured web 1 retains.

The number, spacing, and size of apertures 6 can be varied by changing the shape, number, spacing, orientation and size of teeth 110 and making corresponding dimensional changes as necessary to roll 104 and/or roll 102. This variation, together with the variation possible in precursor webs 20 and the variation in processing, such as line speeds, roll temperature, and other post processing variations, permits many varied apertured webs 1 to be made for many purposes.

First Regions

Referring to FIGS. 1A and 1B, a web 1 according to the present invention comprises a plurality of first regions 8, each of the first regions 8 being surrounded by four distinctive second regions 10. The four distinctive second regions 10 which surround the each of the first regions 8 are connected by two adjacent macro apertures 6 in the first direction and another two adjacent macro apertures 6 in the second direction which is orthogonal to the first direction. The first regions 8 may connect two adjacent macro apertures 6 in the first direction and/or another two adjacent macro apertures 6 in the second direction. In one embodiment, the first regions 8 have a generally quadrilateral shape as shown in FIG. 1B.

Referring to FIG. 1A and FIGS. 2A and 2B, the web of the present invention comprises first regions 8 having a first top plane 9 in a first direction. The first regions 8 and macro apertures 6 form a discontinuous pattern in the first direction and a second direction orthogonal to the first direction. In one embodiment, the flat top plane 9 has an average length no less than 0.9 mm, or no less than 0.95 mm, or no less than 1 mm between two adjacent macro apertures, either in the first direction or in the second direction, as measured according to Top Plane length Measurement.

In one embodiment where a major axis of the macro apertures is substantially parallel to the MD of a web where the macro apertures are formed, and the first regions and the macro apertures form a discontinuous pattern in the MD. In another embodiment where a major axis of the macro apertures is substantially parallel to a CD of a web where the macro apertures are formed.

Second Regions

Referring to FIGS. 1A and 1B, a web 1 according to the present invention comprises a plurality of second regions 10, each of the second regions 10 being surrounded by two adjacent first regions 8 and two adjacent macro apertures 6 located either along a third direction or along a fourth direction which is not parallel either to a first direction or to a second direction orthogonal to the first direction. The second regions 10 and macro apertures 6 form a discontinuous pattern in the third direction and/or in the fourth direction. In one embodiment, the macro apertures 6 and the second regions 10 form a discontinuous pattern between about 30 to about 60 degrees and about 120 to 150 degrees relative to the first direction, or between about 40 to 50 degree and about 140 to 150 degree relative to the first direction, or substantially about 45 degree and about 135 degree relative to the first direction.

Referring to FIGS. 1A and 2C, the web of the present invention comprises second regions 10 having a second top plane 11. A length of the second top plane 11 in the third direction or the fourth direction is longer than a length of the first top plane 9 in the first direction of the first regions 8.

In one embodiment, the second top plane 11 of the second regions has an average length in the third direction or the fourth direction no greater than 0.9 mm, or no greater than 0.85 mm, or no greater than 0.80 mm as measured according to Top Plane length Measurement.

The second regions have better fluid drainage than the first regions, for example, as measured according to Fluid Drainage Test.

Apparatus and Method for Manufacturing Apertured Web

Macro-aperturing the web will increase the fluid handling properties of the web and provide the web with a more cloth-like, fiber-like appearance. Macro apertures in a web can be formed using any processes known in the art. Examples of such processes include but are not limited to the following: vacuum forming, hydroforming, hydrocutting, mechanical deformation, ultrasonics, slitting, ring-rolling, structural elastic-like web, and any combination thereof.

Methods for vacuum formation, hydroforming, mechanical deformation, and ultrasonics are described above. With respect to ultrasonics, additional methods are disclosed in U.S. Pat. Nos. 5,269,981 and 5,269,981. Methods of hydrocutting are disclosed in U.S. Pat. No. 5,567,736. Suitable slitting methods are disclosed in PCT Publication WO 97/31601. In one embodiment, the macro apertures may be formed by a mechanical deformation process. The mechanical deformation process can be carried out on any suitable apparatus that may comprise any suitable type(s) of forming structure. Suitable types of forming structures include, but are not limited to: a pair of rolls that define a nip therebetween; pairs of plates; belts; etc. Using an apparatus with rolls can be beneficial in the case of continuous processes, particularly those in which the speed of the process is of interest. Although the apparatuses will be described herein for convenience primarily in terms of rolls, it should be understood that the description will be applicable to forming structures that have any other suitable configurations.

The rolls for a mechanical deformation process forming the macro apertures described herein are typically generally cylindrical. The term "generally cylindrical", as used herein, encompasses rolls that are not only perfectly cylindrical, but also cylindrical rolls that may have elements on their surface. The term "generally cylindrical" also includes rolls that may have a step-down in diameter, such as on the surface of the roll near the ends of the roll. The rolls are also typically rigid (that is, substantially non-deformable). The term "substantially non-deformable", as used herein, refers to rolls having surfaces (and any elements thereon) that typically do not deform or compress under the conditions used in carrying out the processes described herein. The rolls can be made from any suitable materials including, but not limited to steel, aluminum or rigid plastic. The steel may be made of corrosion resistant and wear resistant steel, such as stainless steel. The rolls may or may not be heated. If heated, consideration of thermal expansion effects must be accommodated according to well known practices to one skilled in the art of thermo-mechanical processes.

The rolls may have any suitable type of elements on their surface (or surface configuration) to form macroscopic apertures, first regions and second regions on a web. The surface of the individual rolls may be provided with forming elements comprising: male elements such as discrete projections and teeth; female elements such as recesses such as discrete voids in the surface of the rolls; or any suitable combination thereof. The female elements may have a bottom surface (which may be referred to as depressions, or cavities), or they may be in the form of apertures (through holes in the surface of the rolls). In some embodiments, the forming elements on the members (such as the rolls) of the forming apparatus may comprise the same general type (that is, the opposing components may both have forming elements thereon, or combinations of forming and mating elements). The forming elements may have any suitable configuration. One type of male elements useful in the present invention are teeth having a base in a generally polygonal shape such as octagonal, hexagonal and quadrilateral shape, and having a cross-sectional length and a cross-sectional width. The teeth have any suitable aspect ratio of its cross-sectional length to its cross-sectional width to form apertures, first regions and second regions on a web. In one embodiment, the teeth have a generally hexagonal shape base. In another embodiment, the teeth have a generally quadrilateral shape base.

The male elements can have tips that are flat, rounded or sharp. In certain embodiments, the shapes of the female elements may differ from the shapes of any mating male forming elements. In certain embodiments, the female forming elements can be configured to mate with one or more male forming elements.

An apertured web according to the present invention can be produced from a three dimensional precursor web having a plurality of discrete extended elements by forming a plurality of discrete extended elements on the precursor web. An apertured web according to the present invention can also be produced from a generally planar, two dimensional precursor web by forming a plurality of discrete extended elements on the precursor web, and forming macro apertures on the precursor web.

One process 150 producing an aperture web is shown schematically in FIG. 4. Precursor web 20 is moved in the machine direction to forming apparatus 100 where apertures 6 are formed producing apertured web 1. Precursor web 20 can be supplied from a supply roll 152 (or supply rolls, as needed for multiple web laminates) or any other supply means, such as festooned webs, as is known in the art. In one embodiment, precursor web 20 can be supplied directly from a web making apparatus, such as a polymer film extruder. Subsequent to formation, apertured web 1 can be taken up on a supply roll 160 for storage and further processing as a component in other products. Alternatively, apertured web 1 can be conveyed directly to further post processing, including a converting operation for incorporation into a finished product, such as a disposable absorbent product.

As shown in FIG. 4, apertured web 1 can be formed from a three dimensional precursor web 20 having, a plurality of discrete extended elements (not indicated in FIG. 4), a first surface 12 and a second surface 14. First surface 12 corresponds to a first side of precursor web 20, as well as a first side of apertured web 1. Second surface 14 corresponds to a second side of precursor web 20, as well as a second side of apertured web 1. In general, the term "side" is used herein in the common usage of the term to describe the two major surfaces of generally two-dimensional webs, such as films. Of course, in a composite or laminate structure, the first surface 12 of the apertured web 1 is the first side of one of the outermost layers or plies, and the second surface 14 is the second side of the other outermost layer or ply.

Supply roll 152 rotates in the direction indicated by the arrow in FIG. 4 as precursor web 20 is moved in the machine direction by means known in the art, including over or around any of various idler rollers, tension-control rollers, and the like (all of which are not shown) to the nip 116 formed by a pair of counter-rotating, intermeshing rolls 102 and 104. The pair of intermeshing rolls 102 and 104 operate to form apertures in web 20 forming apertured web 1. Intermeshing rolls 102 and 104 are more clearly shown in FIG. 5.

Figure 5:
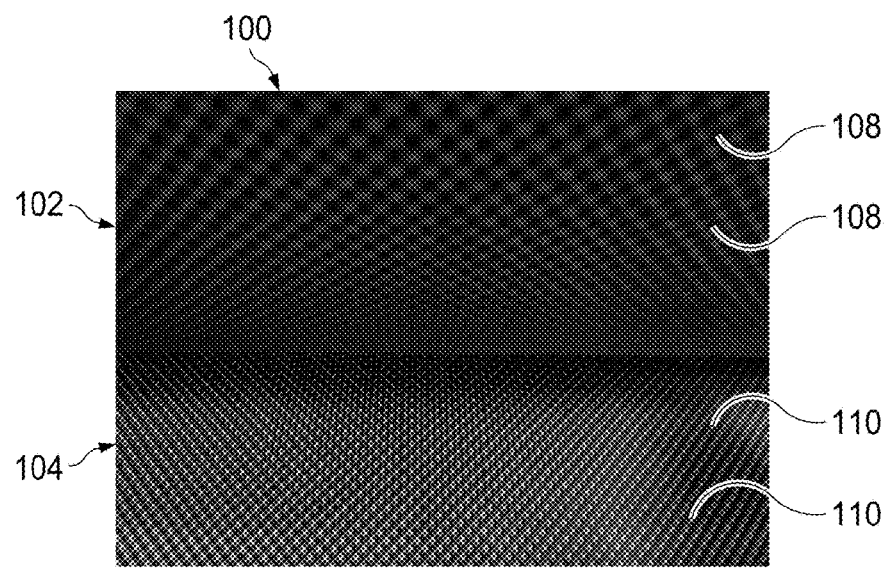
FIG. 5 is a view of intermeshing engagement of portions the apparatus shown of FIG. 4.

Referring to FIGS. 4 and 5, there is shown in more detail the portion of forming apparatus 100 for making apertures in apertured web 1. This portion of apparatus 100 is shown as forming apparatus 100 in FIG. 5, and comprises a pair of intermeshing rolls 102 and 104 rotating in opposite directions. Forming apparatus 100 can be designed such that precursor web 20 remains on roll 104 through a certain angle of rotation. While FIG. 4 shows precursor web 20 going straight into and aperture web 1 coming straight out of nip 116, precursor web 20 or apertured web 1 can be partially wrapped on either of rolls 102 or 104 through a predetermined angle of rotation prior to (for precursor web 20) or after (for apertured web 1) nip 116. For example, after exiting nip 116, apertured web 1 can be directed to be wrapped on roll 104 through a predetermined angle of rotation such that the apertures remain resting over, and "fitted" onto, teeth 110 of roll 104.

Rollers 102 and 104 can be made of steel, aluminum, an alloy metal, and rigid plastic. In general, rollers 102 and 104 can be made of a corrosion resistant and wear resistant metal.

Roll 102 can comprise one or more discrete recesses or voids 108 into which one or more of teeth 110 of roll 104 mesh. The recess 108 may have the same shape as a base of the teeth 110 and slightly larger dimensions on all edges and side than the base of the teeth 110. The depth of the recess may be deeper than a height of the teeth 110. The recess may or may not be tapered. In the case, the spacing of apertures is limited by the spacing of the recesses on roll 102. Thus, it would not be possible to form apertures in the web that have a smaller center-to-center spacing than the center-to-center spacing of the recesses on roll 102. A center-to-center distance of two adjacent apertures is a measure between centers of two adjacent apertures. A point where major axis and a minor axis of an aperture cross each other is determined as a center of the aperture.

Roll 104 comprises a plurality of rows of circumferentially-spaced teeth 110 that extend in spaced relationship about at least a portion of roll 104. Teeth 110 are arranged in a staggered pattern. Teeth 110 extend radially outwardly from the surface of the roll 102 to engage recesses 108 of roll 102. The engagement is shown in greater detail in the cross sectional representation of FIG. 6, discussed below. Both or either of rolls 102 and 104 can be heated by means known in the art such as by incorporating hot oil filled rollers or electrically-heated rollers. Alternatively, both or either of the rolls may be heated by surface convection or by surface radiation.

Teeth 110 can be joined to roller 104. The term "joined to" encompasses configurations in which an element is secured to another element at selected locations, as well as configurations in which an element is completely secured to another element across the entire surface of one of the elements. The term "joined to" includes any known manner in which elements can be secured including, but not limited to mechanical entanglement. Teeth can be attached to, such as by welding, compression fit, or otherwise joined. However, "joined to" also includes integral attachment, as is the case for teeth machined by removing excess material from roller 104. The location at which teeth 110 are joined to roller 104 is the base. At any cross-sectional location parallel to the base each tooth can have a non-round cross-sectional area. In an alternate embodiment the teeth may comprise pins that are rectangular or other shapes depending on the corresponding aperture shape desired.

Figure 6:
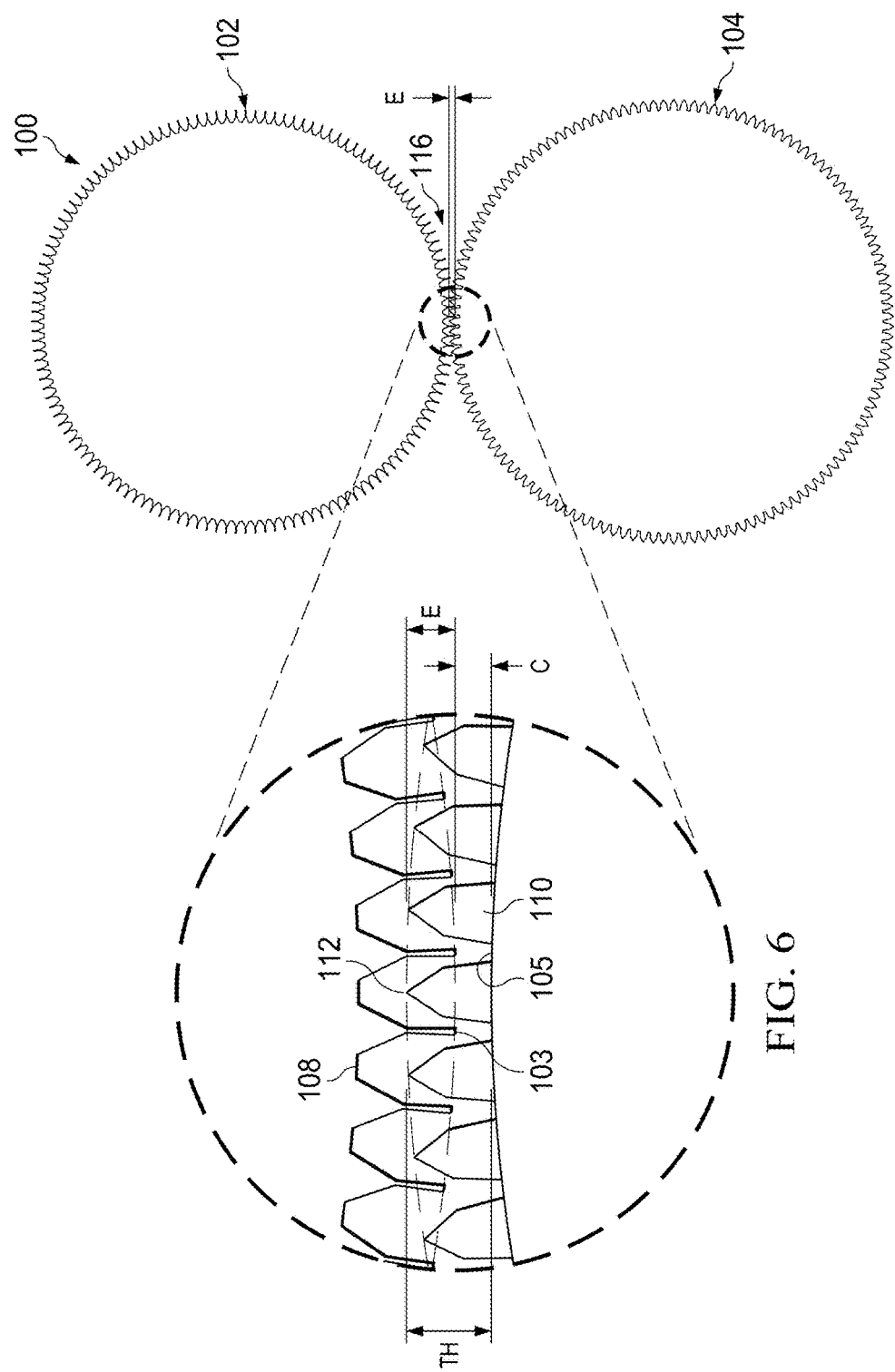
FIG. 6 is a cross-sectional representation of a portion of the apparatus shown of FIG. 5.

FIG. 6 shows in cross section a portion of the intermeshing rolls 102 and 104 including representative teeth 110. As shown, teeth 110 have tooth height TH, depth of engagement E, and gap clearance C. A tooth height TH may range from about 0.5 mm to about 10 mm Depth of engagement E is a measure of the level of engaging rolls 102 and 104 and is measured from a top surface of the roll 102 to tip 102 of tooth 110 of the roll 104. Gap clearance C is a distance between a top surface of the roll 102 and a bottom surface of the roll 104 when rolls 102 and 104 are in maximum engagement. Gap clearance is preferably wide enough to prevent discrete extended elements formed in a precursor web from heat-induced damages from for example a macro aperture forming step, and thus the discrete extended elements remain substantially intact during macro aperture formation process and softness of the web is enhanced. Heat-induced damages include permanent deformation of at least part the discrete extended elements, hardening part of the discrete extended elements as a result of exposure to the heat. Gap clearance preventing discrete extended elements from heat-induced damages can be determined in consideration of precursor web property, precursor web thickness, height of microtextures, macro aperture formation process operation conditions such as roll temperature and production speed. In one embodiment, gap clearance is greater than or equal to the average height of microtextures such as the discrete extended elements formed on the precursor web. In another embodiment, clearance may be no less than about 1.6 mm.

The size and shape of the tooth tip 112 may be specified via the tip radius TR. The depth of engagement E, tooth height TH, Clearance C, and tip radius TR can be varied as desired depending on the properties of precursor web and the desired characteristics of apertured web 1 of the present invention. It is also contemplated that the size, shape, orientation and spacing of the teeth 110 can be varied about the circumference and width of roll 104 to provide for varied apertured web 1 properties and characteristics.

Additionally, substances such as lotions, ink, surfactants, and the like can be sprayed, coated, slot coated, extruded, or otherwise applied to apertured web 1 before or after entering nip 116. Any processes known in the art for such application of treatments can be utilized.

Figure 7A:
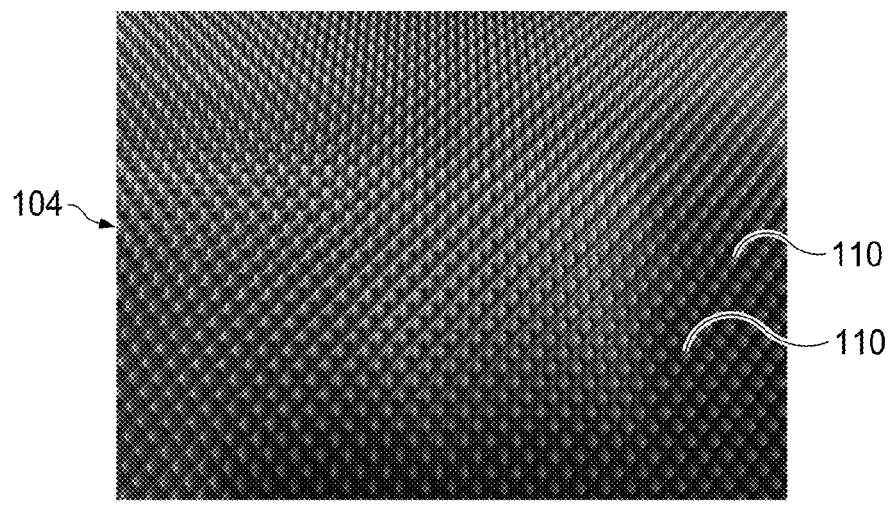
FIG. 7A is a view of a portion of a first member of the apparatus shown of FIG. 5.
Figure 7B:
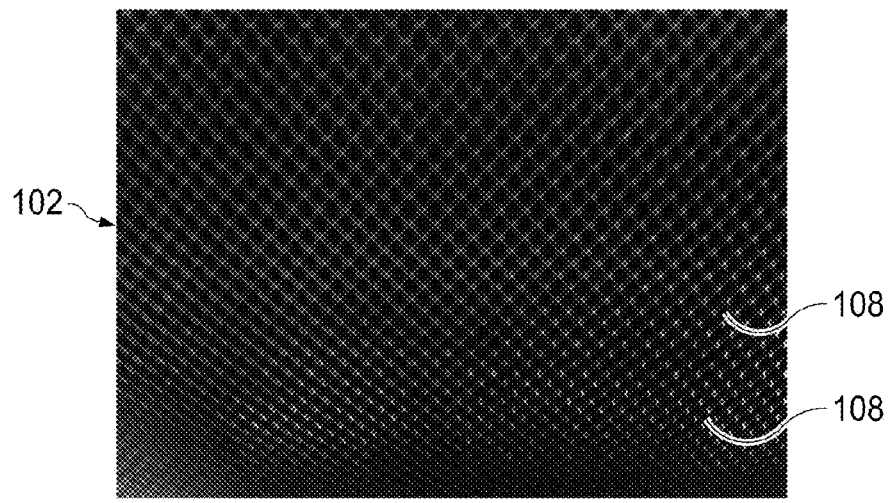
FIG. 7B is a view of a portion of a second member of the apparatus shown of FIG. 5.

FIG. 7A shows a portion of one embodiment of a roller 104 having a plurality of teeth 110 useful for making an apertured web 1. FIG. 7B shows a portion of one embodiment of a roller 102 having a plurality of recesses 108 useful for making an apertured web 1.

Figure 8A:
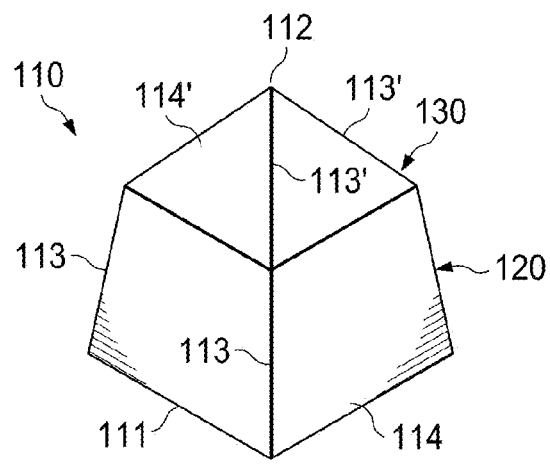
FIG. 8A is a schematic representation of an exemplary tooth of the apparatus shown of FIG. 4.

A perspective view of an exemplary configuration for teeth 100 is shown in FIG. 8A. As shown in FIG. 8A, each tooth 110 has a base 111, a tooth tip 112, edges 113, and sides 114. Teeth 110 can have a base in a generally polygonal shape. As opposed to round, pin-like shapes that are generally round in cross section, teeth 110 can be elongated in one dimension or two dimensions, having generally non-round, elongated cross-sectional configurations. For example, at their base 111, the cross section of teeth 110 can have a tooth cross-sectional length TL and a tooth cross-sectional width TW exhibiting a tooth aspect ratio AR of TL/TW of not greater 3.3, or not greater than 2.5, or not greater than 2, or not greater than 1.9. In one embodiment, each of the teeth has a quadrilateral shape base. The teeth 110 are tapered from a base to a tip in a way that a degree of taper is not constant along the height of the teeth. The tooth 110 may comprise a proximal part 120 joined to a member of a forming apparatus, and a distal part 130 directly adjacent to the proximal part and tapering to a tooth tip 112. The tooth 110 may comprise a proximal part, a distal part, and a middle part between the proximal part 120 and the distal part 130. The proximal part and the distal part may have different degree of taper from each other. In one embodiment, the distal part 130 has a higher degree of taper than the proximal part 120. In another embodiment, at least one of the proximal part 120 and the distal part 130 has a constant degree of taper. The proximal part is generally a fructum shape tapering from a polygonal-shape base to a point. As shown in FIG. 5A, a proximal part 120 can have four sides 114, each side being generally (isosceles) rectangular. The vertex of two sides makes up an edge. The vertices of edges 113 can be relatively sharp, or can be machined to have a rounded radius of curvature. As shown in FIG. 5A, a distal part130 can have a generally pyramid shape having at least four sides 114', each side being substantially triangular and tapering from the bottom of the distal part to a tip of the tooth. The vertex of two sides of the distal part 130 makes up an edge. The vertices of edges 113' can be relatively sharp, or can be machined to have a rounded radius of curvature. The tooth tip 112 can be generally pointed, blunt pointed, or otherwise shaped so as to stretch and/or puncture the precursor web 20. The outermost tips 112 of the teeth have sides that may be rounded to avoid cuts or tears in the precursor material.

In another embodiment, other tooth shapes can be utilized to make apertures. For example, the generally pyramidal shape of distal part 130 shown in FIG. 8A can be truncated so as to remove the pointedness of tips 112 and a flattened region is produced at the distal end of tooth 110. The flattened region can also be elongated, that is, having a length dimension greater than a width dimension and an aspect ratio AR corresponding to the aspect ratio of tooth 110. In one embodiment, a flattened region can transition to sides 114 at generally sharp vertices, or the transition can be at a radius of curvature, providing for a smooth, rounded, flattened tooth tip. Without being bound by theory, it is believed that having relatively sharp tips on teeth 110 permits the teeth 110 to punch through precursor web 20 "cleanly", that is, locally and distinctly, so that the resulting apertured web 1 can be described as being predominantly "apertured" rather than predominantly "embossed". In one embodiment, puncture of precursor web 20 is clean with little deformation of web 20, such that the resulting web is a substantially two-dimensional perforated web.

Figure 8B:
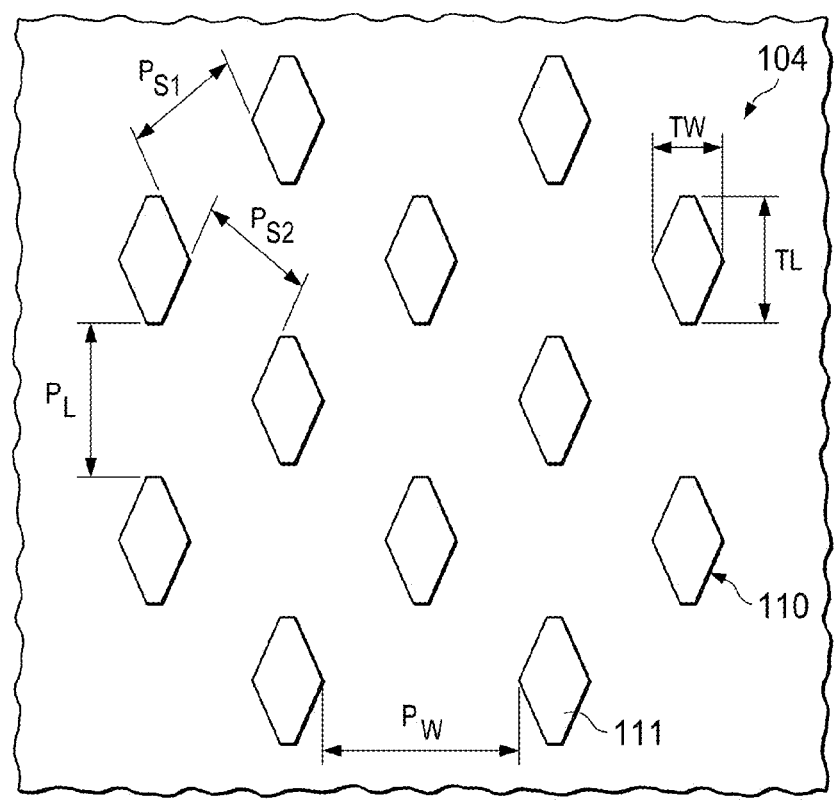
FIG. 8B is a schematic representation of a configuration for another teeth of the apparatus shown of FIG. 4.
Figure 9A:
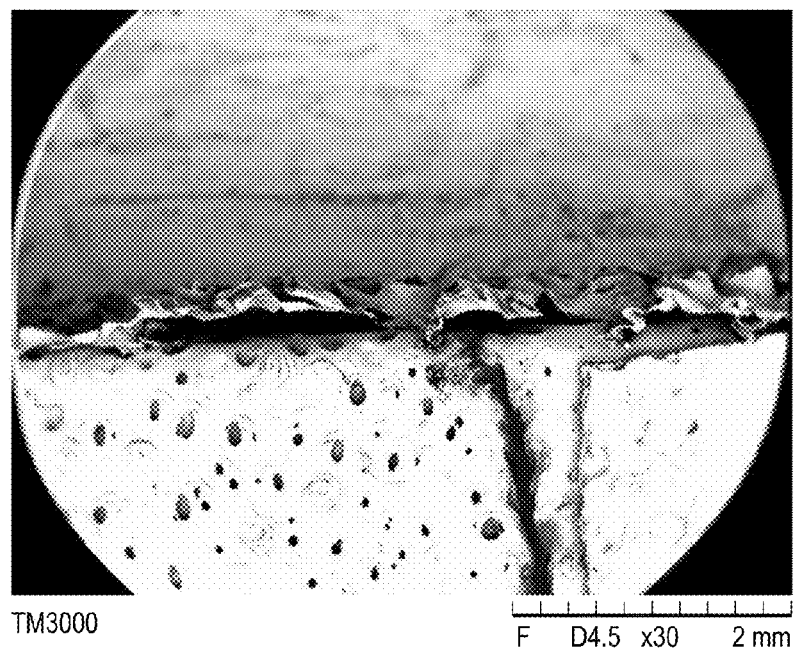
FIG. 9A is a scanning electron microscope image of an A-A direction cross section of the film of FIG. 1C.
Figure 9B:
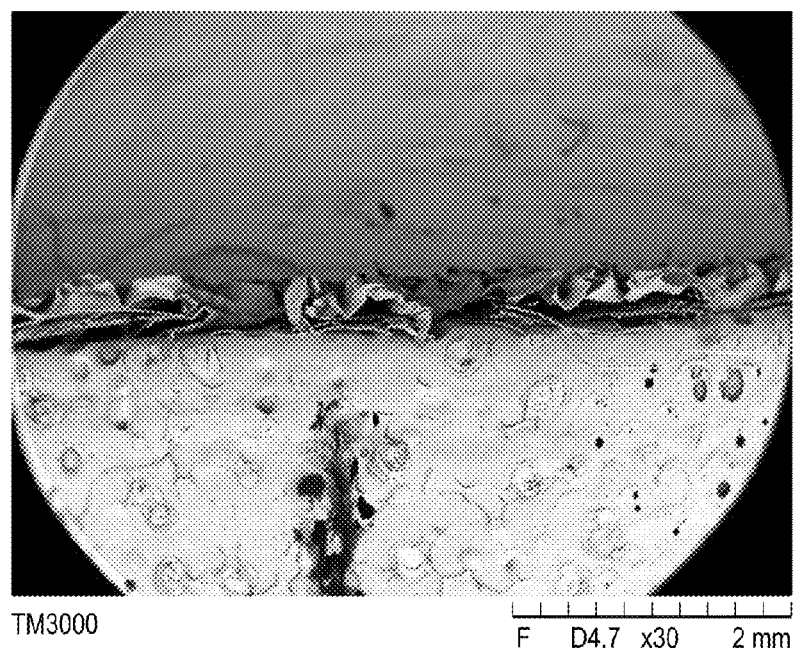
FIG. 9B is a scanning electron microscope image of a B-B direction cross section in cross direction of the film of FIG. 1C.
Figure 9C:
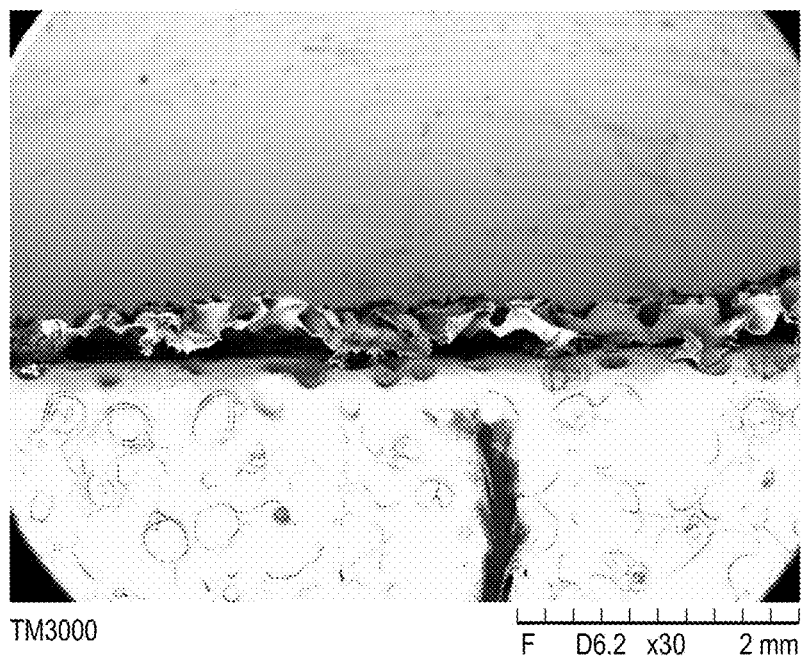
FIG. 9C is a scanning electron microscope image of a C-C direction cross section of the film of FIG. 1C.
Figure 10A:
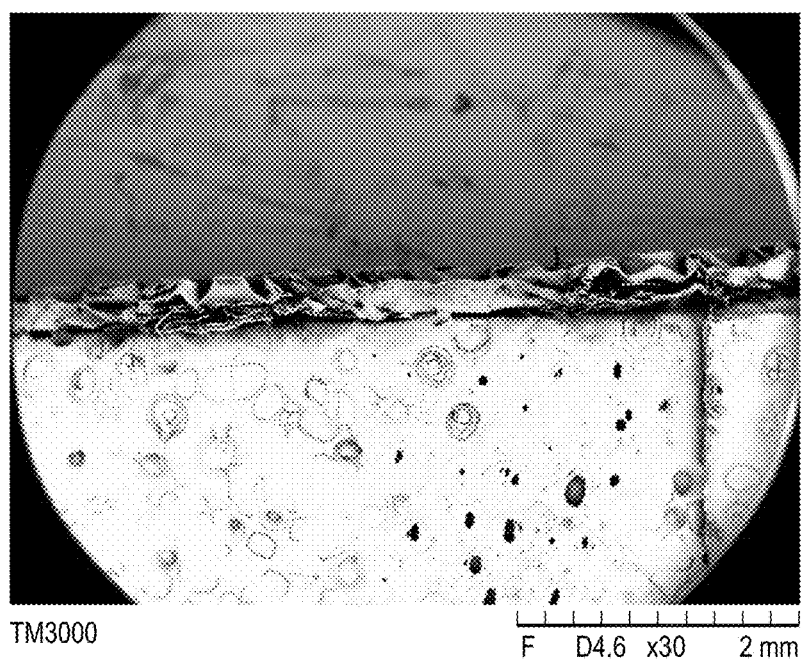
FIG. 10A is a scanning electron microscope image of an A-A direction cross section of the film of FIG. 1D.
Figure 10B:
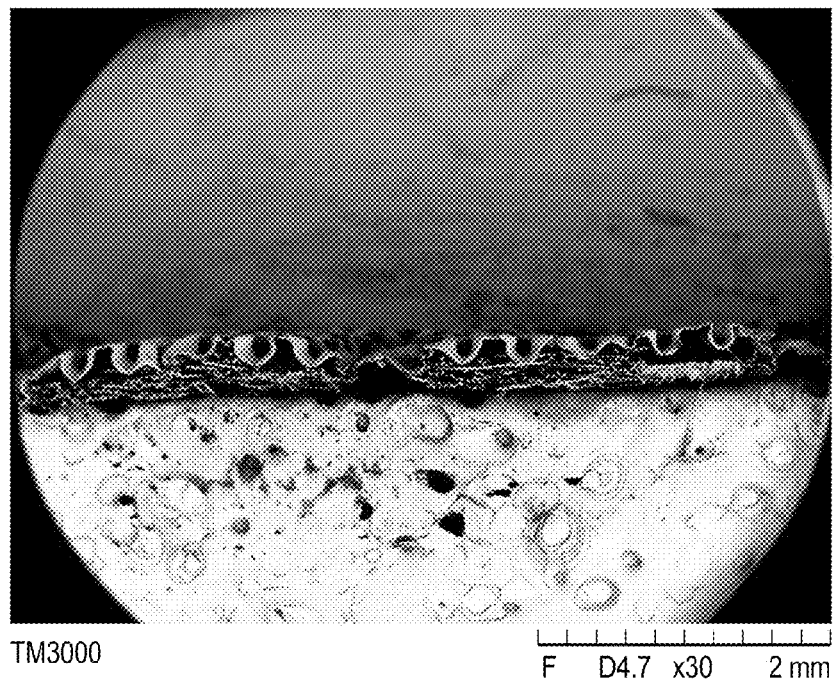
FIG. 10B is a scanning electron microscope image of a B-B direction cross section of the film of FIG. 1D.
Figure 10C:
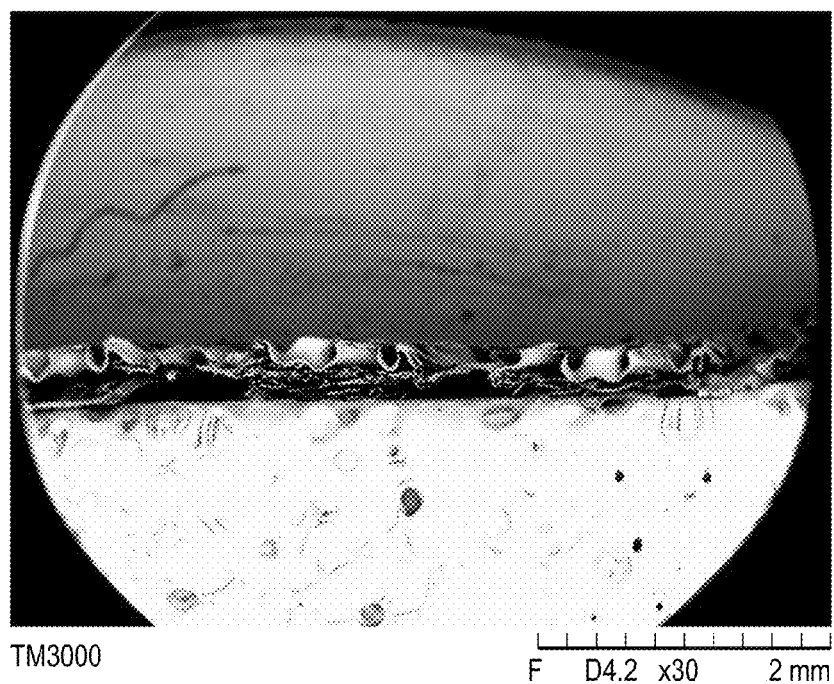
FIG. 10C is a scanning electron microscope image of a C-C direction cross section of the film of FIG. 1D.

Another exemplary configuration for teeth 100 is shown in FIG. 8B. The teeth 110 having a cross sectional length TL and a cross sectional width TW are arranged in a staggered pattern to have a tooth-to-tooth spacing $P_L$ between two adjacent teeth along the cross-sectional length dimension, a tooth-to-tooth spacing $P_W$ between two adjacent teeth along the cross-sectional width dimension, and a tooth-to-tooth spacing $P_S$ between two adjacent teeth along a line that is not parallel either to the cross-sectional length dimension or to the cross-sectional width dimension. The teeth 110 may have different lengths of tooth-to-tooth spacing $P_S$, $P_{S1}$ and $P_{S2}$, depending on teeth configuration. By referring to FIGS. 5A and 5B, in teeth FIG. 5B, the base 111 has a hexagonal shape by slightly cutting out two opposite edges 113 of the proximal part. Edges 113' of the distal part 130 corresponding to the two opposite edges 113 of the proximal part also cut out.

In one embodiment, a tooth-to-tooth spacing $P_S$ between two adjacent teeth along a line that is not parallel either to the cross-sectional length dimension or to the cross-sectional width dimension not greater than or equal to about 1.5 mm. In another embodiment, at least one of the tooth-to-tooth spacing $P_L$ and $P_W$ is greater than about 1.5 mm.

Of course, tooth-to-tooth spacings $P_L$, $P_W$ and/or $P_S$, tooth cross sectional length TL, and tooth cross sectional width TW can each be varied independently.

Application Of Apertured Web

Apertured web can be used in disposable absorbent articles such as bandages, wraps, incontinence devices, diapers, sanitary napkins, pantiliners, tampons, and hemorrhoid treatment pads, as well as other consumer products such as floor cleaning sheets, body wipes, and laundry sheets.

For example, the aperture web of the present invention can be used in applications such as products that contact human or non-human animal skin, such as infant-use disposable diapers, adult-use disposable diapers, sanitary napkins, panty liners, incontinence pads, interlabial pads, breast-milk pads, sweat sheets, animal-use excreta handling articles, animal-use diapers, and similar various absorbent articles; face masks, base fabric of cooling/heating pads and similar cosmetic/medical-use patches, wound surface protection sheets, nonwoven bandages, hemorrhoid pads, warming devices that directly contact the skin (e.g. disposable hand warmers), base fabric of various animal-use patches, and similar skin covering sheets; makeup removal sheets, anti-perspirant sheets, bottom wipes and similar wipes for use on a person, various wiping sheets for use on animals, and the like. The web of the present invention is preferably used as a topsheet for an absorbent article in which the surface of the aperture web 1 having a plurality discrete extended elements is in contact with the skin.

Absorbent Article

An absorbent article according to the present invention comprises a topsheet and a backsheet joined to the topsheet, wherein the topsheet comprises the apertured web according to the present invention. It may further comprise an absorbent core between the topsheet and the backsheet.

The absorbent articles may be produced industrially by any suitable means. The different layers may thus be assembled using standard means such as embossing, thermal bonding, or gluing or combination of both.

Topsheet

With the apertured web according to the present invention, a surface of the web having a plurality discrete extended elements is preferably, disposed on a side in contact with the skin.

Backsheet

Any conventional backsheet materials commonly used for absorbent articles may be used as backsheet. In some embodiments, the backsheet may be impervious to malodorous gases generated by absorbed bodily discharges, so that the malodors do not escape. The backsheet may or may not be breathable.

Absorbent Core

It may be desirable that the article further comprises an absorbent core disposed between the topsheet and the backsheet. As used herein, the term "absorbent core" refers to a material or combination of materials suitable for absorbing, distributing, and storing fluids such as urine, blood, menses, and other body exudates. Any conventional materials for absorbent core suitable for absorbent articles may be used as absorbent core.

Test Methods

Fluid Drainage Test

Artificial Menstrual Fluid Simulant ("AMFS") Preparation

The Artificial Menstrual Fluid Simulant (referred to herein as "AMFS") used in this testing is composed of 70% defibrinated sheep's blood and 30% of a solution comprised of melted gelatin, anionic polyacrylamide flocculant, and phosphate-buffered saline solution. Such an AMFS is described in more detail in U.S. Pat. No. 7,659,372.

The melted gelatin is prepared by combining 7 grams of edible-grade, unflavored gelatin with 85 grams of sterile distilled water. The components are heated and stirred until dissolution. The solution is allowed to solidify in a 4° C. refrigerator overnight. The phosphate-buffered saline solution is prepared by combining 22 grams of a solution containing 0.138% hydrous monobasic sodium phosphate and 0.85% sodium chloride with 70 grams of a solution containing 0.14% of anhydrous dibasic sodium phosphate and 0.85% sodium chloride. The anionic polyacrylamide flocculant, available from Kemira as Superfloc™ A-150, is prepared by combining 1 gram of the flocculant beads with a 1% sodium chloride solution in sterile distilled water. The solution is set at room temperature for one week.

To make 100 ml of AMFS, 7 grams of solidified gelatin is added to 21.5 grams phosphate-buffered saline solution and heated on a hotplate at 35° C. until visually melted. This solution is allowed to cool to 25° C. Then 1.5 grams of anionic polyacrylamide flocculant is added, followed by 70 grams of defibrinated sheep's blood available from Cleveland Scientific. The resulting AMFS is inverted ten times to ensure component mixing and is then placed in a 4° C. refrigerator overnight.

The AMFS viscosity is checked for testing suitability using a TA Instruments AR 1500 or AR 2000 rotational rheometer. After allowing the AMFS batch to warm to 25° C., it is tested at a 25° C. instrument temperature using a steel, 40 mm, 0° plate with a gap 500-1000 microns that ramps shear rate from 0.5 to 30 l/s. Linear regression is applied to the resulting shear curve and the viscosity is calculated for a shear rate of 20 l/s. An AMFS viscosity of 17-23 centipoise at 20 l/s is considered acceptable for use in the test methods herein.

Fluid Drainage a) An absorbent article to be test is unfolded, and removed from all release papers/films/tapes. The absorbent article is flattened and fixed on an A4 paper by using adhesives on the back side of a backsheet of the absorbent article.

b) The absorbent article is placed under an optical microscope such as SZX 12, Olympus optionally equipped with a digital camera. A focal length and a light intensity are adjusted under a total magnification 16×.

c) 2 ml of AMFS prepared according to Artificial menstrual Fluid Simulant ("AMFS") Preparation is applied to a focal point of the absorbent article for about 5 seconds using a pipette. AMFS drainage is recorded by a video connected to the microscope for 3 minutes from the AMFS application.

d) A photo of the absorbent article after 3 seconds from the moment AMSF drainage progress is not observed any more is screened from the recorded video.

Top Plane Length Measurement

Lengths of top planes of first regions and second regions of a web are measured as follows.

Sample Preparation a) A 3×3 $cm^2$ piece is cut from acenter of an absorbent article, and all other components except a topsheet are removed to obtain a sample stripe.

b) A foam container with a flat metal plate at the bottom therein is placed in a heavy metal holder to stably hold the foam container. Liquid nitrogen is filled into the foaming container.

c) The sample stripe prepared in step a) is clamped using a forceps or other convenient tool, and immersed into the liquid nitrogen to freeze the film strip. A blade (Single Edge SS Dispenser Blade, Prod No. 121-22, Ted Pella, Inc., USA) held by a blade holder is immersed into the liquid nitrogen in the container to cool down the blade.

d) When nitrogen boiling stops, the frozen film strip is cut perpendicularly using the blade without any seesaw motion to obtain a cross section of the film strip. The cutting of a film strip is carried out to cross-sect at least two adjacent apertures in the shortest distance between the two adjacent apertures.

e) The cut film strip prepared in step d) is removed from the liquid nitrogen.

Scanning Electron Microscopy ("SEM") Image a) A sample stripe cut to expose a cross-section is fixed to a metal plate by using a carbon double-side tape.

b) SEM Images of cross sections of topsheet strip are taken using SEM such as TM3000, Hitachi (Japan).

Measurement of a Length of a Top Plane

Figure 11:
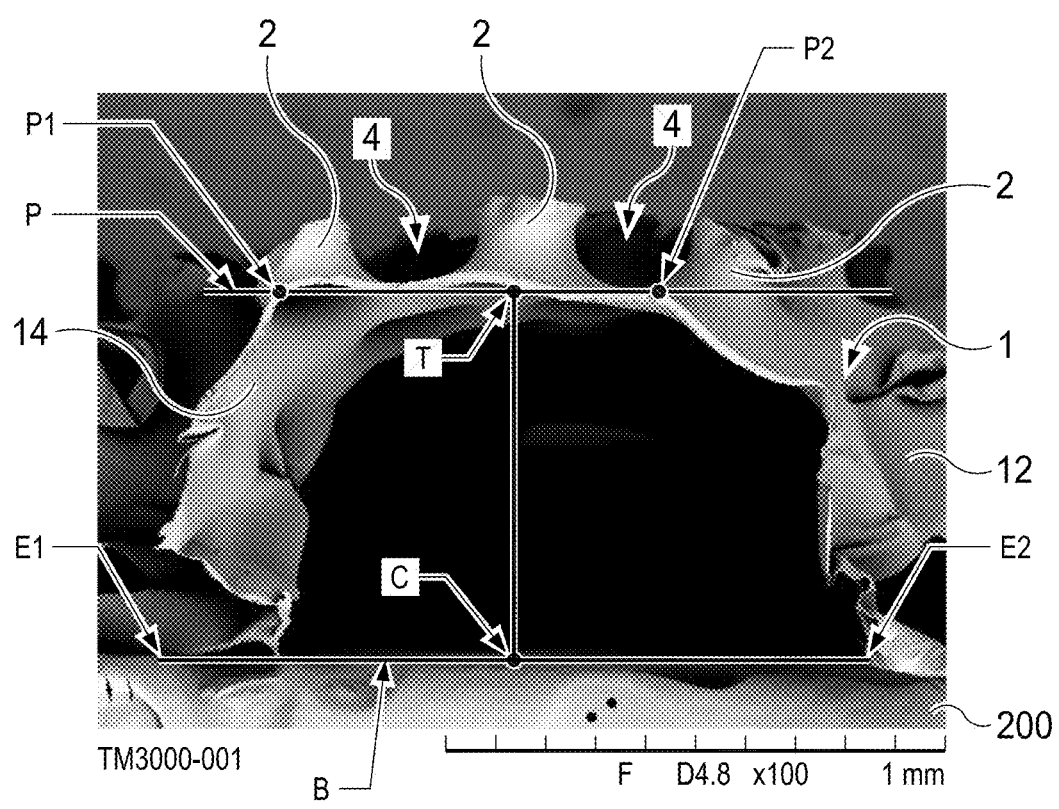
FIG. 11 is a scanning electron microscope image of a cross section of the film of FIG. 1A.

Measurement of a length of a top plane of the first regions and second regions is explained referring to FIG. 11.

a) An end point E1, E2 indicates a point where each of two adjacent macro apertures contacts base surface 200 (amend FIG. 11), or the lowest point of each macro aperture edge if one of the two macro aperture or both macro apertures don't contact the base surface 200. Choose the higher end point between E1 and E2 or choose any of E1 and E2 if E1 and E2 are located in the same height, and draw a horizontal line parallel to the base surface 200 from the chosen end point toward a macro aperture in the other side until the horizontal line hits the macro aperture. This line is determined as a base line B. A contact point on base line B which equally bisects base line B is a center point C.

b) Draw a line perpendicular to the base line B from the center point C toward a top plane of the first or second area of the web 1 until the perpendicular line hits second surface 14 of the web 1. A contact point of the perpendicular line and the second surface 14 of the web 1 is a top plane contact point T.

c) Draw a line P parallel to the base line B from the top plane contact point T extending toward both directions until the line P does not contact valley area 4 among discrete extended elements 2. A contact point of the line P and a web in each side is a plane point P1, P2.

d) A length of the line P between the plane points P1 and P2 is determined as a length L of the top plane of the first area or the second area.

When necessary due to material variability, an average value was measured over a homogenous area of the web.

EXAMPLE

Example 1

Sample Preparation

A non-limiting example of web films according to the present invention was produced by running micro apertured, a 70 mesh poly ethylene film, against forming apparatus of FIGS. 4 and 5 having teeth of FIG. 8B. The teeth are arranged in a staggered pattern, and oriented to having a major axis in a MD and a minor axis in a CD. The film was activated at a temperature of 60-90° C. FIG. 1A is a highly magnified portion of the obtained web film obtained by SEM (TM3000, Hitachi, Japan). Sanitary pads were prepared using the film obtained above as a tophseet.

Example 2

Fluid Drainage Test

Fluid drainage of a pad prepared in Example 1 and commercially available sanitary pads were tested according to Fluid Drainage Test described in TEST METHODS section. Results are shown in FIGS. 3A-3D. As shown, the pad prepared in example 1 exhibits excellent fluid drainage in the second regions.

Example 3

Top Plane Length Measurement

Lengths of top planes of first regions and second regions of films manufactured in Example 1 and commercially available sanitary pads were measured according to Top Plane Length Measurement described in TEST METHODS section. For each of the test samples, lengths of top planes of multiple first regions between two adjacent macro apertures a first direction and another two adjacent macro apertures in a second direction orthogonal to the first direction, and multiple second regions in an angle between two adjacent macro apertures were measured. Average lengths were calculated. Results are summarized in Table 1.

TABLE 1

| Sample | Number of tested first regions in MD | Average length of first regions in | Standard Deviation |
|---|---|---|---|
| Example 1 | 5 | 1.06 | 0.09 |
| Comparative sample 1[*1] | 4 | 1.76 | 0.10 |
| Comparative sample 2[*1] | 4 | 1.68 | 0.55 |
| Comparative sample 3[*3] | 5 | 1.45 | 0.17 |

*[1]Kotex U, Kimberly Clark, Singapore
*[2]: Lilian, Kleannara Co. Ltd, Korea,
*[3]7Space Teens, Hengan Industrial Co. Ltd, China

TABLE 2

| Sample | Number of tested first regions in CD | Average length of first regions in CD | Standard Deviation |
|---|---|---|---|
| Example 1 | 8 | 1.63 | 0.14 |
| Comparative sample 1[*1] | 5 | 0.98 | 0.17 |
| Comparative sample 2[*1] | 6 | 2.37 | 0.04 |
| Comparative sample 3[*3] | 6 | 2.29 | 0.14 |

*[1]Kotex U, Kimberly Clark, Singapore
*[2]: Lilian, Kleannara Co. Ltd, Korea,
*[3]7Space Teens, Hengan Industrial Co. Ltd, China

TABLE 3

| Sample | Number of tested first regions in MD | Average length of first regions in MD | Standard Deviation | T. Test Probability |
|---|---|---|---|---|
| Example 1 | 10 | 0.70 | 0.15 | |
| Comparative sample 1[*1] | 10 | 1.07 | 0.23 | 0.00030 |
| Comparative sample 2[*1] | 10 | 1.45 | 0.14 | 0.00001 |
| Comparative sample 3[*3] | 8 | 1.28 | 0.17 | 0.00048 |

*[1]Kotex U, Kimberly Clark, Singapore
*[2]: Lilian, Kleannara Co. Ltd, Korea,
*[3]7Space Teens, Hengan Industrial Co. Ltd, China The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "90°" is intended to mean "about 90°".

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A web having a first surface and a second surface opposite to the first surface comprising:

a) a plurality of discrete extended elements extending outwardly from the first surface, the discrete extended elements having open proximal ends, open or closed distal ends and side walls,
b) a plurality of macro apertures having a major axis dimension and a minor axis dimension and being arranged in a staggered pattern,
c) a plurality of first regions, each of the first regions being surrounded by four distinctive second regions, the four distinctive second regions being connected by two adjacent macro apertures located in a first direction and another two adjacent macro apertures located in a second direction which is orthogonal to the first direction,
d) a plurality of second regions, each of the second regions being surrounded by two adjacent first regions and two adjacent macro apertures located along a third direction or a fourth direction, wherein the third direction and the fourth direction are not parallel to either the first direction or to the second direction,
wherein the second regions comprise a second top plane having a length less than or equal to about 0.9 mm between the two adjacent macro apertures as measured according to Top Plane length Measurement.

2. The web of claim 1, wherein the web comprises the discrete extended elements selected from discrete extended elements having a diameter of less than about 500 microns, the discrete extended elements having an aspect ratio of at least about 0.2, at least about 95 discrete extended elements per square centimeter, and mixtures of thereof.

3. The web of claim 1, wherein the web comprises the macro apertures with a macro aperture density of from about 20 to about 40 macro aperture/cm² web.

4. The web of claim 1, wherein the discrete extended elements comprises opened distal ends.

5. The web of claim 1, wherein the macro apertures have a ratio of a major axis dimension to minor axis dimension not greater than about 3.3.

6. The web of claim 1, wherein the first top plane has a length greater than about 0.9 mm in at least one of the first direction and the second direction as measured according to Top Plane length Measurement.

7. The web of claim 1, wherein the discrete extended elements are substantially intact.

8. The web of claim 1, wherein the macro apertures have a polygonal shape.

9. The web of claim 1, wherein the macro apertures have a quadrilateral shape.

10. The web of claim 1, wherein the discrete extended elements are formed by a vacuum formation process.

11. The web of claim 1, wherein the macro apertures are formed by a mechanical deformation process.

12. A web having a first surface and a second surface opposite to the first surface comprising:
a) a plurality of discrete extended elements extending outwardly from the first surface, the discrete extended elements having open proximal ends, open or closed distal ends and side walls,
b) a plurality of macro apertures having a major axis dimension and a minor axis dimension and being arranged in a staggered pattern,
c) a plurality of first regions, each of the first regions being surrounded by four distinctive second regions, the four distinctive second regions being connected by two adjacent macro apertures located along a first direction and another two adjacent macro apertures located along a second direction which is perpendicular to the first direction,
d) a plurality of second regions, each of the second regions being surrounded by two adjacent first regions, and two adjacent macro apertures located along a third direction or a fourth direction, wherein the third direction and the fourth direction are not parallel either to the first direction or to the second direction,
wherein the second regions have better fluid drainage than the first regions.

13. The web of claim 12, wherein the fluid drainage is measured according to Fluid Drainage Test.

14. The web of claim 12, wherein the web comprises the discrete extended elements selected from discrete extended elements having a diameter of less than about 500 microns, the discrete extended elements having an aspect ratio of at least about 0.2, at least about 95 discrete extended elements per square centimeter, and mixtures of thereof.

15. The web of claim 1, wherein the discrete extended elements are substantially intact from heat damage.

16. The web of claim 1, wherein the macro apertures have a polygonal shape.

17. The web of claim 1, wherein the macro apertures have a quadrilateral shape.

18. The web of claim 1, wherein the discrete extended elements are formed by a vacuum formation process.

19. The web of claim 1, wherein the macro apertures are formed by a mechanical deformation process.

20. An absorbent article comprising a liquid pervious topsheet comprising;
the web according to claim 1, the tophseet having a body-facing surface and a garment facing surface opposed to the body facing surface, and a liquid impervious backsheet joined to the topsheet.

* * * * *